United States Patent
Suzuki et al.

(10) Patent No.: US 9,757,077 B2
(45) Date of Patent: Sep. 12, 2017

(54) RADIATION IMAGE CAPTURING DEVICE, RADIATION IMAGE CAPTURING METHOD, AND NUCLEAR MEDICINE DIAGNOSIS APPARATUS

(71) Applicant: HITACHI, LTD., Tokyo (JP)

(72) Inventors: Atsuro Suzuki, Tokyo (JP); Yuichiro Ueno, Tokyo (JP); Takafumi Ishitsu, Tokyo (JP); Wataru Takeuchi, Tokyo (JP); Isao Takahashi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 15/038,868

(22) PCT Filed: Oct. 29, 2014

(86) PCT No.: PCT/JP2014/078764
§ 371 (c)(1),
(2) Date: May 24, 2016

(87) PCT Pub. No.: WO2015/079857
PCT Pub. Date: Jun. 4, 2015

(65) Prior Publication Data
US 2016/0374633 A1 Dec. 29, 2016

(30) Foreign Application Priority Data

Nov. 26, 2013 (JP) ................. 2013-244299

(51) Int. Cl.
*G01T 1/20* (2006.01)
*A61B 6/00* (2006.01)
(Continued)

(52) U.S. Cl.
CPC ............ *A61B 6/4435* (2013.01); *A61B 6/037* (2013.01); *A61B 6/06* (2013.01); *A61B 6/4258* (2013.01);
(Continued)

(58) Field of Classification Search
CPC ........................... G01T 1/1648; G01T 1/2985
See application file for complete search history.

(56) References Cited

U.S. PATENT DOCUMENTS 5,838,009 A    11/1998  Plummer et al.
6,211,523 B1 * 4/2001  Gagnon ................ G01T 1/1648
                                                250/363.02
(Continued)

FOREIGN PATENT DOCUMENTS

JP    10-039030 A    2/1998
JP    10-160851 A    6/1998
(Continued)

OTHER PUBLICATIONS

International Search Report of PC/TJP2014/078764 dated Feb. 10, 2015.

*Primary Examiner* — Kho Kim
(74) *Attorney, Agent, or Firm* — Mattingly & Malur, PC

(57) ABSTRACT

When two detector panels are rotationally moved around the entire circumference of a region of interest and projection images of the region of interest are captured during the rotational movement, the respective detector panels are moved along the tangential direction of the rotational movement to a position where the union of the capturing ranges of the projection images captured by the respective detector panels covers the entire region of interest. The projection images captured by the respective detector panels are used to reconstruct a transaxial image of the region of interest.

14 Claims, 13 Drawing Sheets

(51) Int. Cl.
*G01T 1/164* (2006.01)
*G01T 1/29* (2006.01)
*A61B 6/03* (2006.01)
*A61B 6/06* (2006.01)

(52) U.S. Cl.
CPC .......... *A61B 6/4266* (2013.01); *A61B 6/4417* (2013.01); *A61B 6/4452* (2013.01); *A61B 6/50* (2013.01); *A61B 6/503* (2013.01); *A61B 6/5205* (2013.01); *G01T 1/1641* (2013.01); *G01T 1/1644* (2013.01); *G01T 1/2985* (2013.01); *A61B 6/5258* (2013.01)

(56) References Cited

U.S. PATENT DOCUMENTS

| | | | | |
|---|---|---|---|---|
| 6,359,279 B1 * | 3/2002 | Gagnon | ................ | G01T 1/1648 250/360.1 |
| 6,628,983 B1 * | 9/2003 | Gagnon | ................ | G01T 1/1648 600/431 |
| 2014/0014828 A1 * | 1/2014 | Bredno | ................ | A61B 6/032 250/252.1 |

FOREIGN PATENT DOCUMENTS

| | | |
|---|---|---|
| JP | 2000-221271 A | 8/2000 |
| JP | 2001-343462 A | 12/2001 |
| JP | 2004-037418 A | 2/2004 |
| JP | 2009-031306 A | 2/2009 |

\* cited by examiner (a)

(b)

(a)

(b)

(a)

(b)

RADIATION IMAGE CAPTURING DEVICE, RADIATION IMAGE CAPTURING METHOD, AND NUCLEAR MEDICINE DIAGNOSIS APPARATUS

TECHNICAL FIELD

The present invention relates to a radiation image capturing device, a radiation image capturing method, and a nuclear medicine diagnosis apparatus that are suitable for medical applications.

BACKGROUND ART

Techniques for applying a radiation measurement apparatus to nuclear medicine include a single photon emission computed tomography (hereinafter referred to as "SPECT") using a gamma camera. The SPECT measures the distribution of a compound including a radioisotope and provides a tomographic plane image. The mainstream type of the conventional SPECT system is a type of apparatus formed by combining a scintillator consisting of one crystal plate with a plurality of photomultiplier tubes. The position of a radiation source in this type of SPECT system can often be calculated by, e.g., centroid calculation. However, the maximum resolution achieved by such calculation is approximately 10 mm, which is not sufficient to satisfy the requirements of the clinical setting.

In response, a pixelated detector extremely advantageous for enhancement of spatial resolution has been developed. Some pixelated detectors are composed of a scintillator, and other types are composed of a semiconductor. A positional signal of the radiation source acquired by any type of detector is on a small detector basis, in other word, on a pixel basis. The intrinsic spatial resolution of the detector is determined by the pixel size. Detectors with a pixel size of 1 to 2 mm have been developed. Since resolution of 10 mm or below has been achieved, detectors have been significantly improved.

New image reconstruction methods for a tomographic plane have been developed and improved to contribute to resolution enhancement. The Filtered Back-Projection (FBP) method and successive approximation methods without resolution recovery (such as the Maximum Likelihood Expectation Maximization (MLEM) method, and the Ordered Subset Expectation Maximization (OSEM) method). Recent years have seen development of a successive approximation method with a resolution recovery feature. This method enables reconstruction of a tomographic plane considering the geometry of a collimator or detector, attenuation of a gamma ray by the object, a scattered ray, and other physical factors.

Types of SPECT systems include entire body capturing apparatuses whose capturing range is wide enough to cover the entire body, dedicated cardiac and brain capturing apparatuses specialized for the brain and the heart, and dedicated cardiac capturing apparatuses specialized for the heart. Most widespread SPECT systems are entire body capturing apparatuses that can perform bone imaging by capturing the entire body. However, the quality of brain and heart images captured by an entire body capturing apparatus is inferior to the quality of images captured by, e.g., dedicated cardiac and brain capturing apparatuses specialized for capturing only the brain and the heart. Accordingly, there is a call for a SPECT system that can not only perform entire body capturing, but also capture images of the heart, the brain, and other organs whose quality is as good as the image quality of dedicated cardiac and brain capturing apparatuses.

PTL 1 and PTL 2 disclose the technique for capturing, e.g., SPECT images using a small-area radiation detector. For example, PTL 1 discloses that the detector is moved in the tangential direction of the rotational path of the detector so that the region of interest of the capturing target (e.g., the heart) is in the capturing range of the detector at each rotational position of the detector. Also, PTL 1 discloses that by changing the position of the detector between the first rotation and the second rotation in the tangential direction of the rotation path of the detector, the region of the heart is contained in the capturing range of the detector. Also, PTL 2 discloses that each of a plurality of small-area detectors is disposed to cover a region outside the capturing range of another region, whereby the entire body of the object is captured.

CITATION LIST

Patent Literature

PTL 1: JP 10-39030 A
PTL 2: JP 2009-31306 A

SUMMARY OF INVENTION

Technical Problem

However, in the case of PTL 1 where the detector is moved at each rotational position in the tangential direction to capture the region of interest, the capturing range of the detector needs to be longer than the region of interest. Also, PTL 1 discloses that when the capturing range of the detector is shorter than the region of interest, the position of the detector in the tangential direction can be differentiated between the first and second rotations by moving the detector twice around the object (region of interest). In such a situation, depending on the position of the region of interest, such as the heart, regions of no interest (e.g., non-heart portions)—in other words, an unnecessary region—tend to account for a large portion in a captured transaxial image. In the method of PTL 2, an unnecessary region eventually accounts for a large portion of a transaxial image.

When a region of no interest accounts for a large portion in a captured transaxial image, the region of interest becomes relatively small. The number of counts by a radiation detector from the region of interest decreases, and the quality of a captured image of the region of interest deteriorates.

An object of the present invention is to provide a radiation image capturing device, a radiation image capturing method, and a nuclear medicine diagnosis apparatus that can increase the number of counts by a radiation detector from the region of interest, which is the capturing target, and enhance the quality of a captured image of the region of interest.

Solution to Problem

A radiation image capturing device according to the present invention includes: a detector panel including a collimator that aligns an incident direction of a radioactive ray and a detector that detects the radioactive ray, the incident direction of which is aligned by the collimator; a gantry mounted with one or a plurality of the detector panels, the gantry performing a rotational movement of the mounted detector panel around a circumference, an object being substantially a center of the circumference; and a tangential direction moving mechanism that moves, in a tangential direction of the rotational movement, the one detector panel or the plurality of the detector panels mounted on the gantry, wherein when the gantry performs the rotational movement of the one detector panel or the plurality of the detector panels around the entire circumference of the object and a projection image of the region of interest at each rotational position is captured by the one detector panel or the plurality of the detector panels, the one detector panel or each of the plurality of the detector panels is moved in the tangential direction so that a size of a union of a capturing range of the projection image captured by the one detector panel or each of the plurality of the detector panels corresponds to a size of the region of interest, and the projection image captured by the one detector panel or each of the plurality of the detector panels that have performed the rotational movement and the tangential direction movement is used to reconstruct a transaxial image of the region of interest.

Advantageous Effects of Invention

According to the present invention, it is possible to provide a radiation image capturing device, a radiation image capturing method, and a nuclear medicine diagnosis apparatus that can increase the number of counts by a radiation detector from the region of interest, which is the capturing target, and enhance the quality of a captured image of the region of interest.

BRIEF DESCRIPTION OF DRAWINGS

FIG. 3(a) is a diagram illustrating the situation of acquiring a projection image by the detector panel $d_1$, and FIG. 3(b) is a diagram illustrating the situation of acquiring a projection image by the detector panel $d_2$.

FIG. 4(a) is an example where the detector panel $d_1$ is positioned at the center of the capturing range. FIG. 4(b) is an example where the detector panel $d_1$ is moved toward an end portion on the positive direction side of the capturing range. FIG. 4(c) is an example where the detector panel $d_2$ is moved toward an end portion on the negative direction side of the capturing range. FIG. 4(d) is an example situation where the detector panels $d_1, d_2$ have an overlapping captured region.

FIG. 7(a) is an upper surface diagram, and FIG. 7(b) is a side surface diagram.

FIG. 9(a) is a diagram illustrating an example situation of acquiring a gamma ray projection image using four small-area detector panels according to the modified embodiment of the first embodiment. FIG. 9(b) is a diagram illustrating an example situation of acquiring a gamma ray projection image using two large-area detector panels according to a comparative embodiment.

FIG. 15(a) illustrates an example transaxial image, and FIG. 15(b) illustrates an example projection image.

FIG. 16(a) illustrates an example transaxial image containing the heart and the liver; FIG. 16(b) illustrates an example projection image that can be acquired from the transaxial image of the heart; and FIG. 16(c) illustrates an example projection image that can be acquired from the transaxial image of the liver.

FIG. 18(a) is a diagram illustrating that the two detector panels $d_1, d_2$ are moved, respectively, to the position where the region of interest is maximum in the positive direction and to the position where the region of interest is minimum in the negative direction. FIG. 18(b) is a diagram illustrating that the two detector panels $d_1, d_2$ are moved, respectively, to the position where the region of interest is minimum in the negative direction and to the position where the region of interest is maximum in the positive direction.

FIG. 19(a) illustrates the positions of the detector panels $d_1,d_2$ at the beginning of capturing, and FIG. 19(b) illustrates the positions where the detector panels $d_1,d_2$ have rotated to their respective maximum angles.

DESCRIPTION OF EMBODIMENTS

Figure 1:
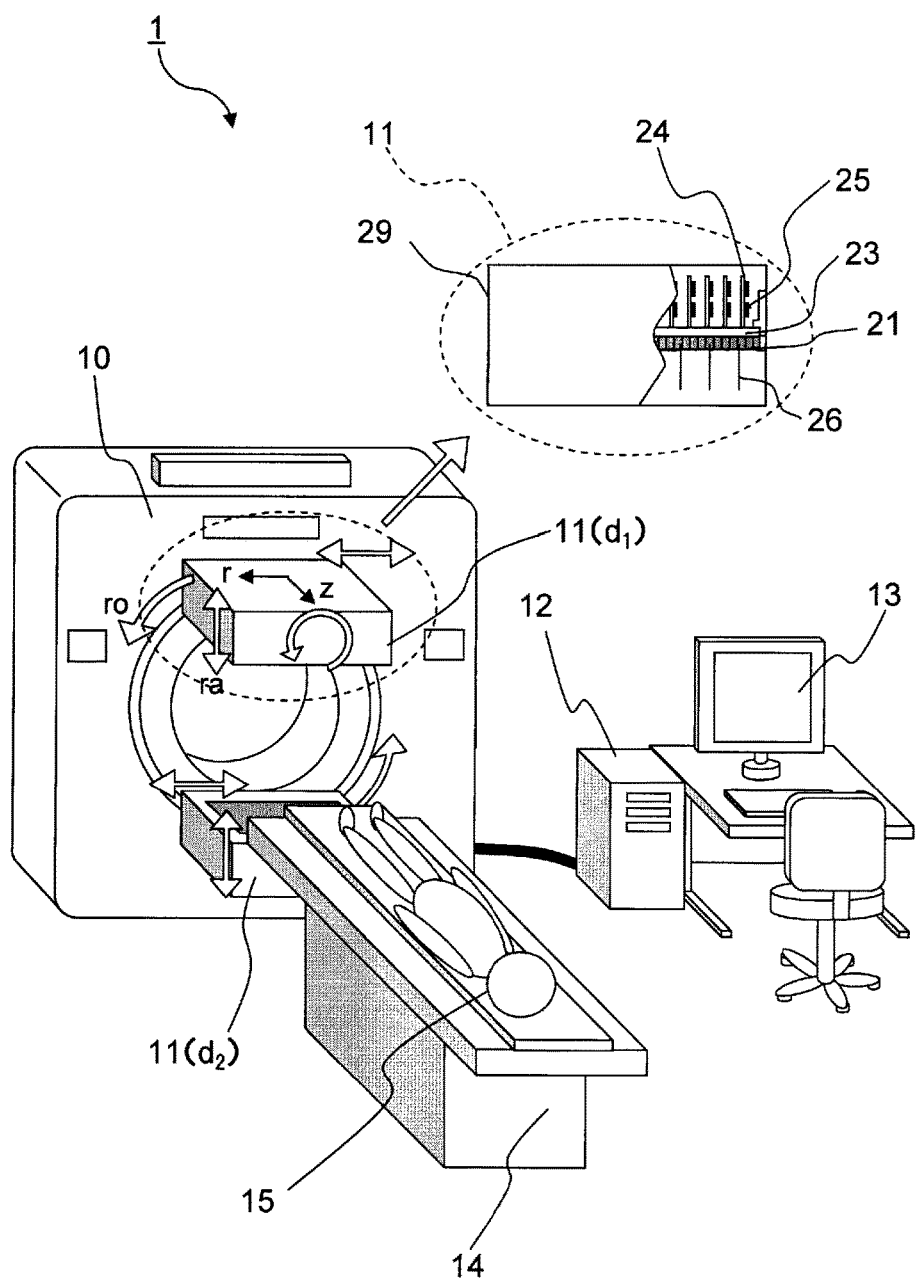
FIG. 1 is a diagram that schematically illustrates an example overall configuration of a SPECT system according to an embodiment of the present invention.

Embodiments of the present invention are hereinafter illustrated in detail by referring to the drawings:

First Embodiment

FIG. 1 is a diagram schematically illustrating an example overall configuration of a SPECT system 1 according to an embodiment of the present invention. As illustrated in FIG. 1, the SPECT system 1, which is a nuclear medicine diagnosis apparatus, includes an annular gantry 10, two detector panels 11 ($d_1,d_2$) disposed so as to oppose to the gantry 10, a data processing device 12, and a display device 13. An object 15 is administered with a radioactive drug (for example, a medical agent containing $^{99m}Tc$ whose half-life period is six hours). A gamma ray released from $^{99m}Tc$ in the body of the object 15 on a bed 14 is detected by the two detector panels 11($d_1,d_2$).

As illustrated in the schematic cross-sectional diagram in the ellipse drawn by the dashed line on the upper right portion of FIG. 1, a shield case 29 of the detector panel 11, in an inside thereof, includes: a pixelated detector 21 constituted by arranging gamma ray detectors on a detector substrate 23 in a planar array form; a collimator 26 for gamma ray incidence aligned with the direction of each gamma ray detector arranged in the aforementioned form; an integrated circuit (ASIC: Application Specific Integrated Circuit) 25 that processes a gamma ray detection signal detected by each gamma ray detector; and an ASIC substrate 24 mounted with the integrated circuit 25. The shield case 29 is made of iron and lead and shields, inter alia, an electromagnetic wave, light, a gamma ray, and the like coming from the outside. However, the surface of the shield case 29 opposite to the object 15 is either open or formed of a material that does not shield a gamma ray.

The gantry 10 with an annular rotating portion is accompanied with a moving mechanism whereby the detector panel 11 freely moves in a radius direction $r_a$, the rotational direction $r_o$, and the tangential direction r of rotation of the gantry 10 as well as in the body axis direction z of the object 15. When the detector panel 11 captures a transaxial image of the object 15, the detector panel 11 rotates along the annular rotational portion of the gantry 10 and detects, in a 360-degree direction, a gamma ray released from the object 15 that has been carried into the inside of the gantry 10 (more specifically, a radioactive drug accumulated in a tumor, etc. in the inside of the object 15).

From among gamma rays released from the inside of the object 15, only a gamma ray from a certain direction is selected by the collimator 26 and detected by each gamma ray detector of the pixelated detector 21. A gamma ray detection signal detected by each gamma ray detector is input into the integrated circuit 25 and converted into peak value data. The peak value data of the gamma ray is associated with the identification number (often referred to as "channel ID") of the detection time of the gamma ray detector having detected the gamma ray, compiled as packet data, and transmitted to the data processing device 12.

The data processing device 12 incorporates the packet data containing the gamma ray peak value, the channel ID, and the detection time that is transmitted from the integrated circuit 25. Subsequently, the data processing device 12 generates a plane image (planar image) or converts the aforementioned data into sinogram data to generate a transaxial image and in turn display the image on the display device 13. The data processing device 12 can be composed of an ordinary computer including a central processing device and a storage device.

When the pixelated detector 21 is angled with respect to the object 15 subject to measurement, the number of counts $y_i$ of a gamma ray detected by a detector i (detector i hereinafter refers to a gamma ray detector that is identified by channel ID=i and constitutes the pixelated detector 21) is given by equation (1) with respect to the number of counts $\lambda_j$ of a gamma ray generated from the object 15 corresponding to a reconstructed pixel j:

$$y_i = \Sigma C_{ij} \lambda_j \quad (1)$$

where $C_{ij}$ denotes the probability that the gamma ray generated from the object 15 corresponding to the reconstructed pixel j is detected by the detector i.

A transaxial image of the object 15 can be reconstructed using a publically known successive approximation reconstruction method (the MLEM method, the OSEM method, etc.). Specifically, in the successive approximation reconstruction method, by incorporating the point response function of the detector into the successive approximation reconstruction scheme, the spatial resolution can be corrected successively. The point response function is the probability that a gamma ray generated from a point or line source is detected by the detector i, which is equal to the detection probability $C_{ij}$ of equation (1). Use of this point response function enables accurate reconstruction of a transaxial image of the object 15 by the successive approximation reconstruction method, such as the MLEM or OSEM method.

Figure 2:
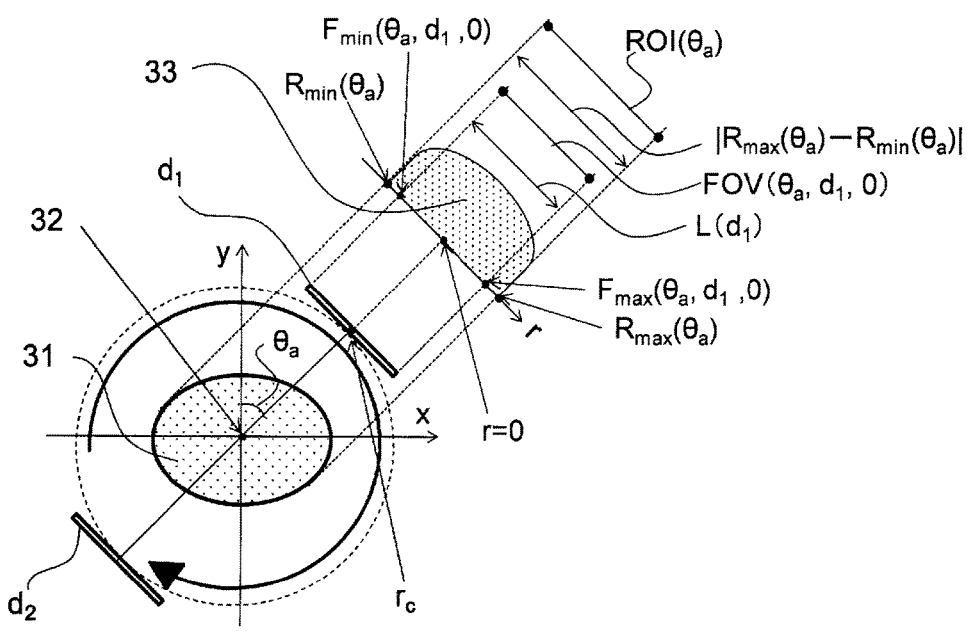
FIG. 2 is a diagram illustrating an example of projection image acquisition using two small-area detector panels.

FIG. 2 is a diagram illustrating an example situation of acquiring a projection image using the two small-area detector panels $d_1,d_2$. By referring to, e.g., FIG. 2 and subsequent FIGS. 3(a) and 3(b), a method of enhancing the detection accuracy by moving the detector panels $d_1,d_2$ in the tangential direction r of the rotation path considering the range of the projection image 33 of the region of interest 31 of the object 15.

As illustrated in FIG. 2, when the detector panels $d_1,d_2$ rotate, the angle between the vertical line running down from the rotation axis 32 to the detector panel $d_1$ and the y axis (vertical direction) is defined as the rotational position $\theta$. The rotational position $\theta$ of one of the detector panels, which is the detector panel $d_1$, is $\theta_a$. The other detector panel, which is the detector panel $d_2$, is disposed to be opposite to the detector panel $d_1$, and the rotational position $\theta$ of the detector panel $d_2$ is $\theta_a+180$.

Here, the rotational positions $\theta$ at the initial state of the detector panels $d_1,d_2$ are 0 degree and 180 degrees, respectively. The detector panels $d_1,d_2$ detect a gamma ray while rotating 360 degrees around the region of interest 31. The tangential direction of the path while the detector panels $d_1,d_2$ are rotating is denoted by r, and the intersection between the vertical lines running down from the rotation axis 32 to the detector panels $d_1, d_2$ is defined as the center (r=0). The center illustrated in FIG. 2, r=0, is an equivalent of $r_c$=0 where $r_c$ denotes the center position of the detector panel $d_1$.

The positions where the size of a projection image of the region of interest 31 at position $\theta_a$ of the detector panel $d_1$ is maximum and minimum in the tangential direction r are denoted by $R_{min}(\theta_a)$ and $R_{max}(\theta_a)$, respectively. The range of this projection image is given by $ROI(\theta_a)=[R_{min}(\theta_a),R_{max}(\theta_a)]$. When the center position $r_c$ of the detector panel $d_1$ is moved from the center (r=0) by $\delta r_i$ in the tangential direction r (FIG. 2 is equivalent to the situation of $\delta r_1$=0), the positions where the capturing range of the detector panel $d_i$ (i=1, 2) is minimum and maximum are denoted by $F_{min}(\theta_a,d_i,\delta r_i)$ and $F_{max}(\theta_a,d_i,\delta r_i)$, respectively, and the corresponding capturing ranges are given by $FOV(\theta_a,d_i,\delta r_i)=[F_{min}(\theta_a,d_i,\delta r_i),F_{max}(\theta_a,d_i,\delta r_i)]$.

$\delta r_i$ can be a positive or negative value. The length of the capturing range of the detector panel $d_i$ in the tangential direction r without respect to the rotational position $\theta_a$ and $\delta r_i$ is given by $L(d_i)=|F_{max}(\theta_a,d_i,\delta r_i)-F_{min}(\theta_a,d_i,\delta r_i)|$. As illustrated in FIG. 2, $L(d_1)$ is shorter than the length ($=|R_{max}(\theta_a)-R_{min}(\theta_a)|$) of $ROI(\theta_a)$ in the tangential direction r, and a truncation error occurs. A SPECT image acquired in the aforementioned situation is inaccurate.

According to this embodiment, a means for moving the detector panels $d_1,d_2$ in the tangential direction r is provided so that the detector panels $d_1,d_2$ can entirely cover $ROI(\theta_a)$. In this case, the sum of the lengths of the detector panels $d_1,d_2$ in the tangential direction r, ($L(d_1)+L(d_2)$), is assumed to be longer than the maximum length of $ROI(\theta)$ in the tangential direction r, ($=|R_{max}(\theta_a)-R_{min}(\theta_a)|$).

Figure 3:
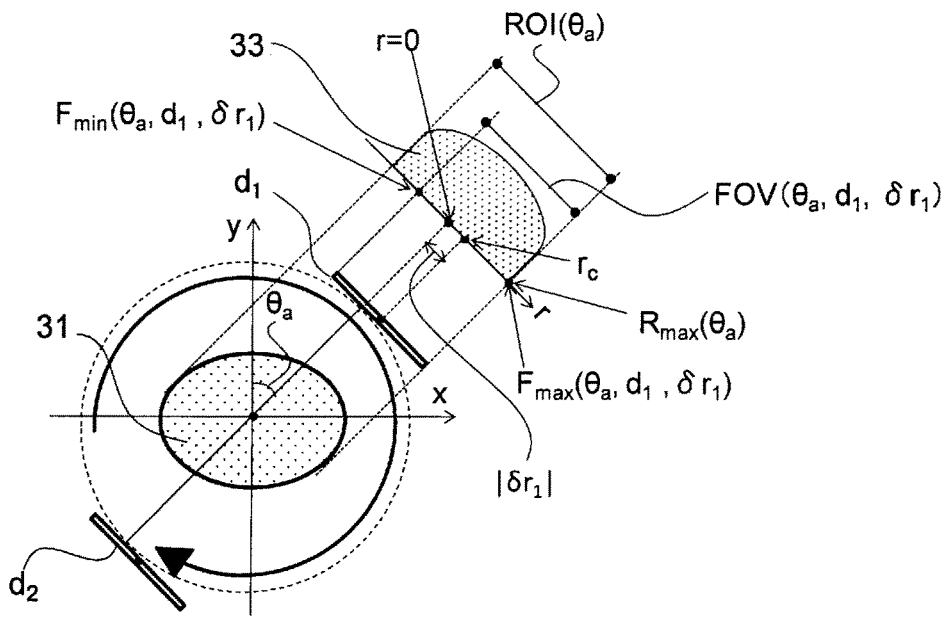
FIGS. 3(a) and 3(b) represent diagrams illustrating situations of acquiring a gamma ray projection image when the detector panels $d_1, d_2$ are moved in the tangential direction r of rotation.
Figure 3:
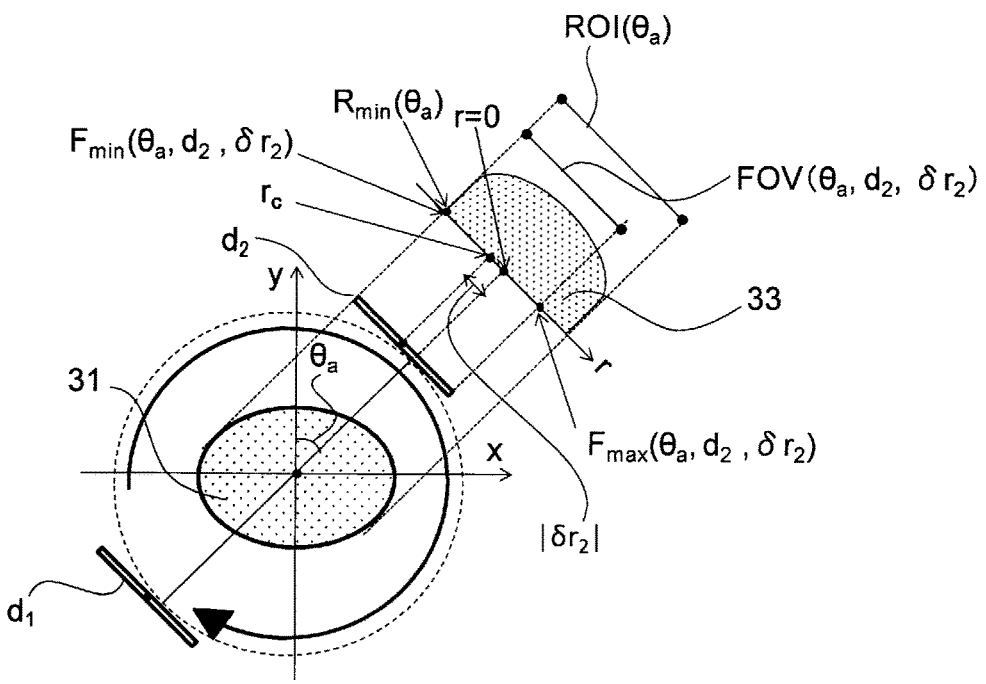

FIGS. 3(a) and 3(b) represent diagrams illustrating the situation of acquiring a projection image when the detector panels $d_1,d_2$ are moved in the tangential direction r of rotation. FIG. 3(a) is a diagram illustrating the situation of acquiring a projection image by the detector panel $d_1$, and FIG. 3(b) is a diagram illustrating the situation of acquiring a projection image by the detector panel $d_2$. As illustrated in FIG. 3(a), the position where the capturing range of the detector panel $d_1$ at the rotational position $\theta_a$ is maximum in the tangential direction r is $F_{max}(\theta_a,d_1,\delta r_1)$, and the center position $r_c$ of the detector panel $d_1$ is moved from the center (r=0) by $\delta r_1$ in the tangential direction r so that $F_{max}(\theta_a,d_1,\delta r_1)$ is positioned near $R_{max}(\theta_a)$. $\delta r_1$ is given by equation (2):

$$\delta r_1 = R_{max}(\theta) - L(d_1)/2 \qquad (2)$$

Specifically, by moving the center position $r_c$ of the detector panel $d_1$ from the center (r=0) by $\delta r_1$ in the tangential direction r, the detector panel $d_1$ can perform capturing the range of $[R_{min}(\theta_a,d_1,\delta r_1),F_{max}(\theta_a)]$ in $ROI(\theta_a)$.

As illustrated in FIG. 3(b), the position where the capturing range of the detector panel $d_2$ at the rotational position $\theta_a$ is maximum in the tangential direction r is $F_{min}(\theta_a,d_2,\delta r_2)$, and the center position $r_c$ of the detector panel $d_2$ is moved from the center (r=0) by $\delta r_2$ in the tangential direction r so that $F_{min}(\theta_a,d_2,\delta r_2)$ is positioned near $R_{min}(\theta_a)$. $\delta r_2$ is given by equation (3):

$$\delta r_2 = R_{min}(\theta) + L(d_2)/2 \qquad (3)$$

Specifically, by moving the center position $r_c$ of the detector panel $d_2$ from the center (r=0) by $\delta r_2$ in the tangential direction r, the detector panel $d_2$ can perform capturing the range of $[F_{min}(\theta_a,d_2,\delta r_2),R_{max}(\theta_a)]$ in $ROI(\theta_a)$.

By combining detection data of the detector panels $d_1,d_2$, a projection image for the entire range $ROI(\theta_a)$ can be acquired. In the capturing ranges of the detector panels $d_1,d_2$ for their respective $ROI(\theta_a)$, an overlapping region $[F_{min}(\theta_a,d_1,\delta r_1),F_{max}(\theta_a,d_2,\delta r_2)]$ exists. In this overlapping region, the chance of gamma ray detection is doubled. The detection accuracy is higher than the accuracy of detecting a gamma ray by one large-area detector.

Figure 4:
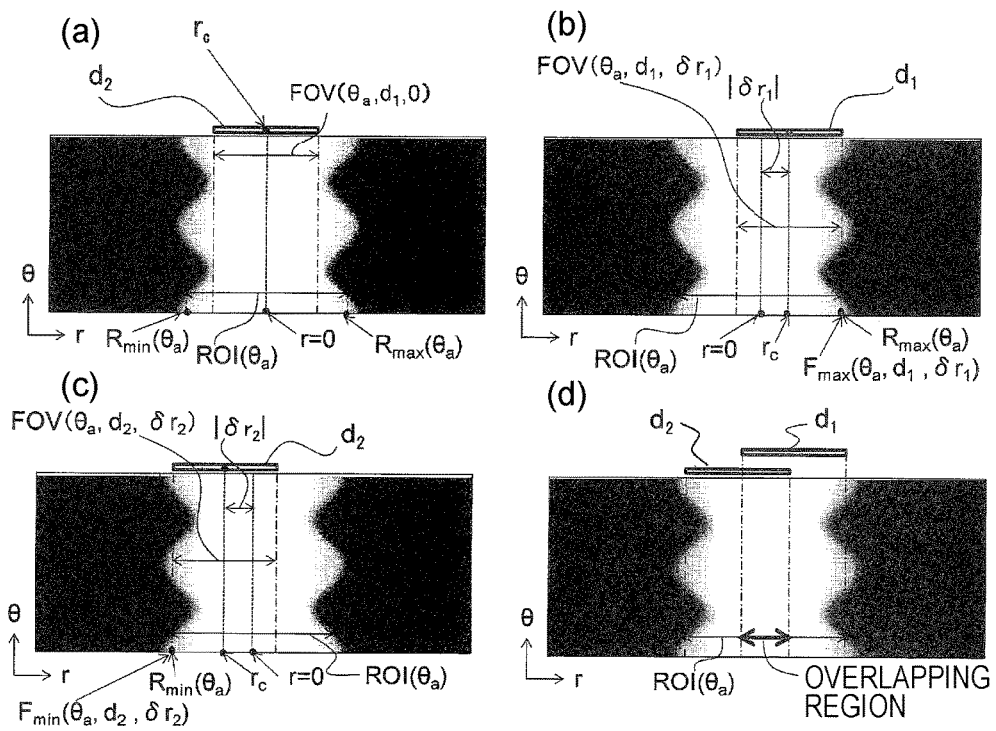
FIGS. 4(a) to 4(d) represent diagrams illustrating relationships between projection image data of the region of interest and the positions of the detector panels $d_1, d_2$.

FIGS. 4(a) to 4(d) represent diagrams illustrating relationships between projection image data of the region of interest 31 and the positions of the detector panels $d_1,d_2$. FIG. 4(a) is an example where the detector panel $d_1$ is positioned at the center of the capturing range. FIG. 4(b) is an example where the detector panel $d_1$ is moved toward an end portion on the positive direction side of the capturing range. FIG. 4(c) is an example where the detector panel $d_2$ is moved toward an end portion on the negative direction side of the capturing range. FIG. 4(d) is an example situation where the detector panels $d_1,d_2$ have an overlapping capturing range. FIGS. 4(a) to 4(d) illustrate the same projection image in a sinogram form where the horizontal axis represents the position in the tangential direction r and the vertical axis represents rotational position $\theta$. The white portion of the projection image in a sinogram form is the region of interest 31.

The aforementioned projection image in a sinogram form can be acquired by, e.g., capturing using an X-ray CT apparatus. In such a case, the X-ray CT apparatus acquiring a projection image is different from the SPECT system 1 according to this embodiment. However, the SPECT system 1 according to this embodiment can be assumed as a SPECT-CT apparatus. In such a case, the SPECT system 1 embedded with an X-ray CT apparatus alone can acquire a projection image by X-ray CT.

In addition, when the SPECT system 1 is not embedded with an X-ray CT apparatus, as long as the sum of the lengths of the detector panels $d_1,d_2$ of the SPECT system 1 in the tangential direction r, which is ($L(d_1)+L(d_2)$), is sufficiently greater than the maximum value of the length of $ROI(\theta)$, ($=|R_{max}(\theta)-R_{min}(\theta)|$), the SPECT system 1 alone can acquire the same projection image.

According to this embodiment, as illustrated in FIG. 4(a), the length of the detector panel $d_1$ in the tangential direction r is $FOV(\theta_a,d_1,\delta r_1)$, which is smaller than the maximum length ($ROI(\theta_a)$) of the tangential direction r in the region of the projection image where pixel values exist (white pixel region). When the center position $r_c$ of the detector panel $d_1$ is positioned at the center (r=0) in the tangential direction r, the capturing range of the detector panel $d_1$, $FOV(\theta_a,d_1,0)$, cannot cover the entire region of interest 31.

According to this embodiment, the two detector panels $d_1$, $d_2$ are used to acquire a projection image of the entire region of interest 31 as illustrated below. For this purpose, the data processing device 12 uses projection image data in a sinogram form that can be acquired from an X-ray CT apparatus, etc. to calculate $\delta r_1$, $\delta r_2$, by the amount of which the detector panels $d_1,d_2$, respectively, are moved from the center (r=0) in the tangential direction r at each rotational position $\theta$ of the detector panels $d_1,d_2$.

Specifically, the data processing device 12 calculates, for each rotational position $\theta$, $ROI(\theta_a)=[R_{min}(\theta_a),R_{max}(\theta_a)]$, which is the range of the projection image of the region of interest 31, as the respective minimum and maximum coordinate values in the tangential direction r of a region where the pixel value of the projection image exceeds the specified threshold value. For example, the data processing device 12 scans, in the direction from r=−∞ to the positive side, a pixel value of the projection image at the rotational position $\theta$ and acquires, as $R_{min}(\theta_a)$, the coordinate value in the tangential direction r when the pixel value exceeds the specified threshold value. Likewise, the data processing device 12 scans, in the direction from r=+∞ to the negative side, the pixel value of the projection image at the rotational position $\theta_a$ and acquires, as $R_{max}(\theta_a)$, the coordinate value in the tangential direction r when the pixel value exceeds the specified threshold value.

In turn, the data processing device 12 uses aforementioned ROI $(\theta_a)=[R_{min}(\theta_a),R_{max}(\theta_a)]$ and equations (2) and (3) to calculate $\delta r_1$, $\delta r_2$, by the amount of which the detector panels $d_1,d_2$, respectively, are moved from the center (r=0).

As illustrated in FIG. 4(b), the center position $r_c$ of the detector panel $d_1$ is moved by $|\delta r_1|$ from the center (r=0) to the positive tangential direction r so that the end portion $F_{max}(\theta_a, d_1, \delta r_1)$ of the capturing range $FOV(\theta_a,d_1,\delta r_1)$ of the detector panel $d_1$ in the positive tangential direction r covers the end portion $R_{max}(\theta_a)$ in the positive direction of ROI$(\theta_a)$. Likewise, as illustrated in FIG. 4(c), the center position $r_c$ of the detector panel $d_2$ is moved by $|\delta r_2|$ from the center (r=0) to the negative tangential direction r so that the end portion $F_{min}(\theta_a,d_2,\delta r_2)$ of the capturing range $FOV(\theta_a, d_2,\delta r_2)$ of the detector panel $d_2$ in the negative tangential direction r covers the end portion $R_{minx}(\theta_a)$ in the negative direction of ROI$(\theta_a)$.

As illustrated in FIG. 4(d), by combining the capturing range $FOV(\theta_a,d_1,\delta r_1)$ of the detector panel $d_1$ and the capturing range $FOV(\theta_a,d_2,\delta r_2)$ of the detector panel $d_2$, ROI$(\theta_a)$ of the entire region of interest 31 is covered. As a result, the data processing device 12 uses the detector panels $d_1,d_2$ to acquire projection image data at each of the rotational positions θ from 0 to 360 degrees and combines the data to acquire projection image data that covers ROI(θ) of the entire region of interest 31.

Figure 5:
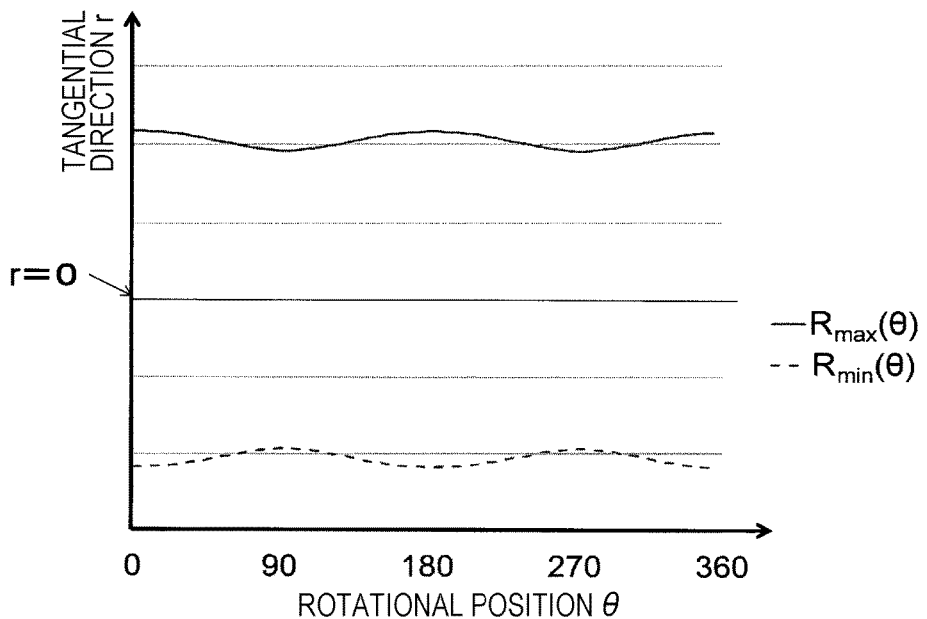
FIG. 5 is a diagram illustrating an example relationship between rotational position θ and the positions of $R_{max}(\theta)$ and $R_{min}(\theta)$, where ROI(θ) that can be acquired from the projection image data illustrated in FIGS. 4(a) to 4(d) is maximum and minimum, respectively.

FIG. 5 is a diagram illustrating an example relationship between the rotational position θ and the positions of $R_{max}(\theta)$ and $R_{min}(\theta)$ where ROI(θ) that can be acquired from the projection image data illustrated in FIGS. 4(a) to 4(d) is maximum and minimum, respectively. Specifically, the solid line of the graph in FIG. 5 represents the maximum position $R_{max}(\theta)$ of ROI(θ), and the dashed line of the graph therein represents the minimum position $R_{min}(\theta)$ of ROI(θ).

Figure 6:
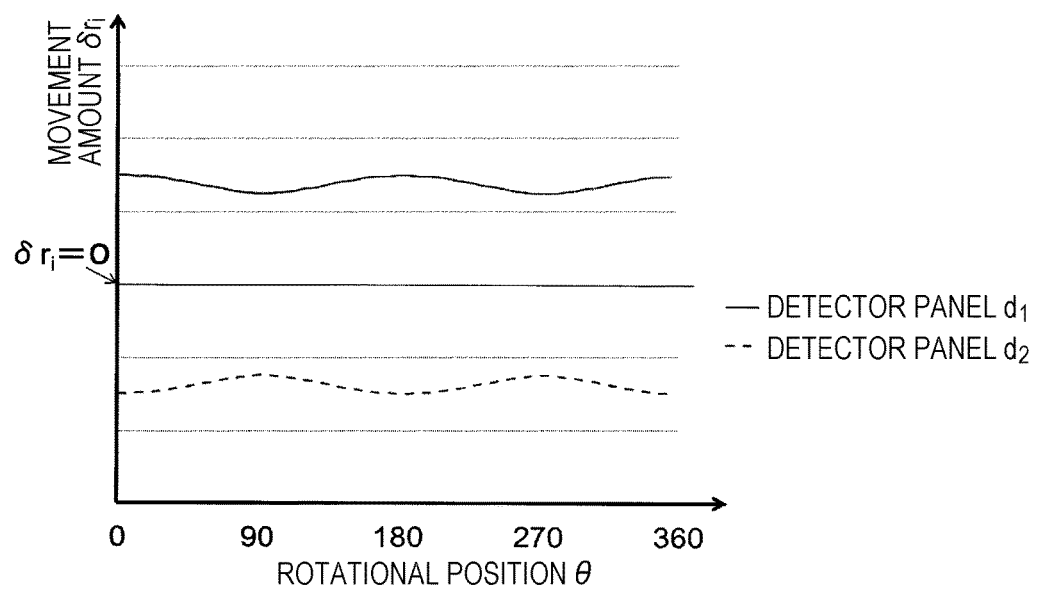
FIG. 6 is a diagram illustrating an example relationship between the rotational position θ and movement amounts $\delta r_1$ and $\delta r_2$ of the detector panels $d_1, d_2$ that can be acquired from length $L(d_1)$ and length $L(d_2)$ of the detector panels $d_1, d_2$, respectively, in the tangential direction r as well as from the graph of FIG. 5.

FIG. 6 is a diagram illustrating an example relationship between the rotational position θ and the movement amounts $\delta r_1$ and $\delta r_2$ of the detector panels $d_1,d_2$ that can be acquired from length $L(d_1)$ and length $L(d_2)$ of the detector panels $d_1,d_2$, respectively, in the tangential direction r as well as from the graph of FIG. 5. The solid line of the graph in FIG. 6 represents the movement amount $\delta r_1$ of detector panel $d_1$, and the dashed line of the graph therein represents the movement amount $\delta r_2$ of detector panel $d_2$.

As described above, according to this embodiment, from projection image data in a sinogram form (see FIGS. 4(a) to 4(d)) acquired in advance, the data processing device 12 calculates, for each rotational position θ, $R_{min}(\theta)$ and $R_{max}(\theta)$, where the range of the projection image of the region of interest is minimum and maximum, respectively, in the tangential direction r (see FIG. 5). Prior to capturing a SPECT image, the data processing device 12 calculates, from $R_{min}(\theta)$ and $R_{max}(\theta)$ thus calculated and equations (2) and (3), the movement amounts $\delta r_1,\delta r_2$ at each rotational position θ illustrated in FIG. 6

In an actual medical setting, the cross-sectional area of the region of interest 31 is different in each slice of the body axis direction. The rotational position θ and the movement amounts $\delta r_1,\delta r_2$ of detector panels $d_1, d_2$ are calculated for each slice in the body axis direction. For each slice at each rotational position θ, the maximum value of $\delta r_1$ and the minimum value of $\delta r_2$ are calculated. When a SPECT image is captured, the maximum value of $\delta r_1$ and the minimum value of $\delta r_2$ are used as the common movement amounts $\delta r_1,\delta r_2$ for each slice of the body axis direction.

As described above, according to this embodiment, the capturing range of the two detector panels $d_1,d_2$ at each rotational position θ is represented by union $FOV(\theta, d_1,\delta r_1) \cup FOV(\theta,d_2,\delta r_2)$ of the capturing range $FOV(\theta,d_1,\delta r_1)$ of the detector panel $d_1$ and the capturing range $FOV(\theta,d_2,\delta r_2)$ of the detector panel $d_2$, which covers the ROI(θ) in its entirety. In this case, a part of ROI(θ) is overlapped when captured by the two detector panels $d_1,d_2$. As the volume of information of the overlapped portion, which is a foundation for SPECT image reconstruction, is doubled, the quality of a SPECT image is enhanced.

Subsequently, the text to follow illustrates timing of moving the detector panels $d_1,d_2$ in the tangential direction r when the region of interest 31 is captured by the detector panels $d_1,d_2$ in the SPECT system 1. The detector panels $d_1,d_2$ repeatedly move and stop in the rotational direction and captures the region of interest 31 in the Step & Shoot mode. In this mode, the detector panels $d_1,d_2$ are moved in the tangential direction r during the rotational movement. Alternatively, the detector panels $d_1,d_2$ may be set so that the detector panels $d_1,d_2$ are moved in the tangential direction r after the rotational movement of the detector panels $d_1,d_2$ stops. In the Continuous mode where the detector panels $d_1,d_2$ continuously rotate for capturing, the detector panels $d_1,d_2$ are continuously moved in the tangential direction r.

Also, the detector panels $d_1,d_2$ may be set to capture the region of interest 31 of the object 15 at each rotational position θ while the detector panels $d_1,d_2$ move in the direction toward the rotational center. In this case, since the detector panels $d_1,d_2$ can be brought as close as possible to the object 15, the detection sensitivity of the detector panels $d_1,d_2$ and the spatial resolution increase.

The method of FIGS. 4(a) to 4(d) for acquiring projection image data of the region of interest 31 is hereinafter further illustrated. As described above, the projection image data of the region of interest 31 is often acquired using an X-ray CT apparatus, but an MRI (Magnetic Resonance Imaging) apparatus may be used for acquisition. At present, as SPECT-CT apparatuses are spreading, the ease of use of an X-ray CT apparatus is higher than that of an MRI apparatus. The advantages of an MRI apparatus include freedom from exposure to radiation, and future emergence of a SPECT-MRI is expected. The aforementioned modalities are effective means for acquisition of a projection image of the region of interest 31.

The advantages of a capturing apparatus, such as an X-ray CT or MRI apparatus, include the ability to acquire not only projection data of the body surface of the object 15, but also a projection image of the internal portion of the object 15, such as the heart or the liver. In such a case, for example, a projection image captured by an X-ray CT apparatus may be used as-is as projection image data of the body surface of the object 15. After binarization is performed by means of division of a reconstructed image into regions, it is possible to use projection data that can be acquired by performing a projection operation for the images of the divided regions. The projection operation refers to forward projection performed for, e.g., successive approximation reconstruction.

In this case, in order to acquire projection data of the internal portion of the object 15, such as the heart or the liver, captured projection data is reconstructed, the region of interest 31 is divided into regions, and projection operation is performed for images of the divided regions.

Figure 7:
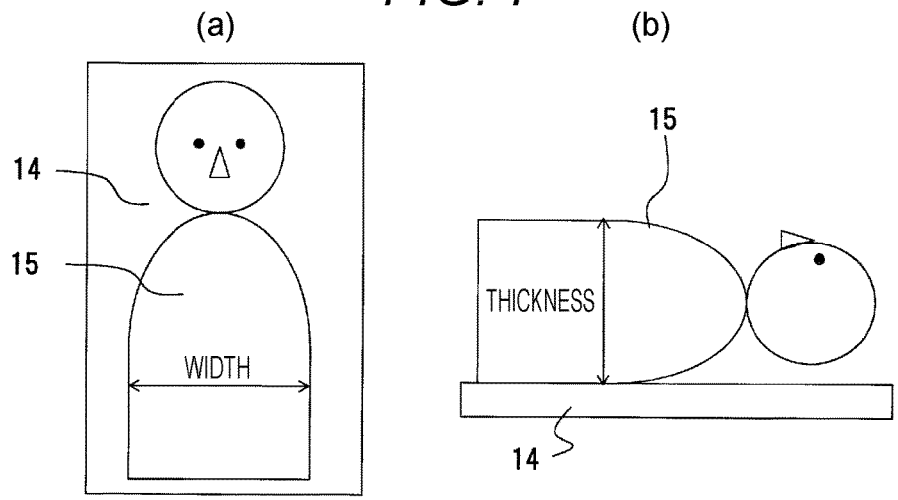
FIGS. 7(a) and 7(b) represents diagrams schematically illustrating situations where an object is lying on a bed.

An optical measuring method may be used to acquire only the range of a projection image of the body surface of the object 15. It is possible to use projection image data acquired by approximating the body surface of the object 15 as an ellipsoid and performing a projection operation for the approximated image based on such information as the height, weight, chest, and abdominal girth of the object 15 as well as the width (see FIG. 7(a)) and thickness (see FIG. 7(b)) of the object 15 lying on the bed 14.

As projection image data, data acquired by SPECT capturing during a short period of time may be used. Alternatively, it is possible to use projection data acquired by approximating the body surface as a circle or ellipsoid and performing a projection operation for the approximated image based on an image acquired by planar image capturing using the detector panels $d_1, d_2$ of the SPECT system 1.

According to this embodiment, the range of a projection image of the region of interest 31 is calculated from projection data. Information used for calculating the range of the region of interest 31 is not limited to projection data, and the range may be calculated from other types of information. For example, when the range of region of interest 31 in the tangential direction r is calculated for the rotational position θ, it is possible to perform coordinate conversion of the rotational angle θ for the region of interest 31 and identify a region where a distribution exists in the direction of the coordinate axis orthogonal to the direction of converted image projection.

Figure 8:
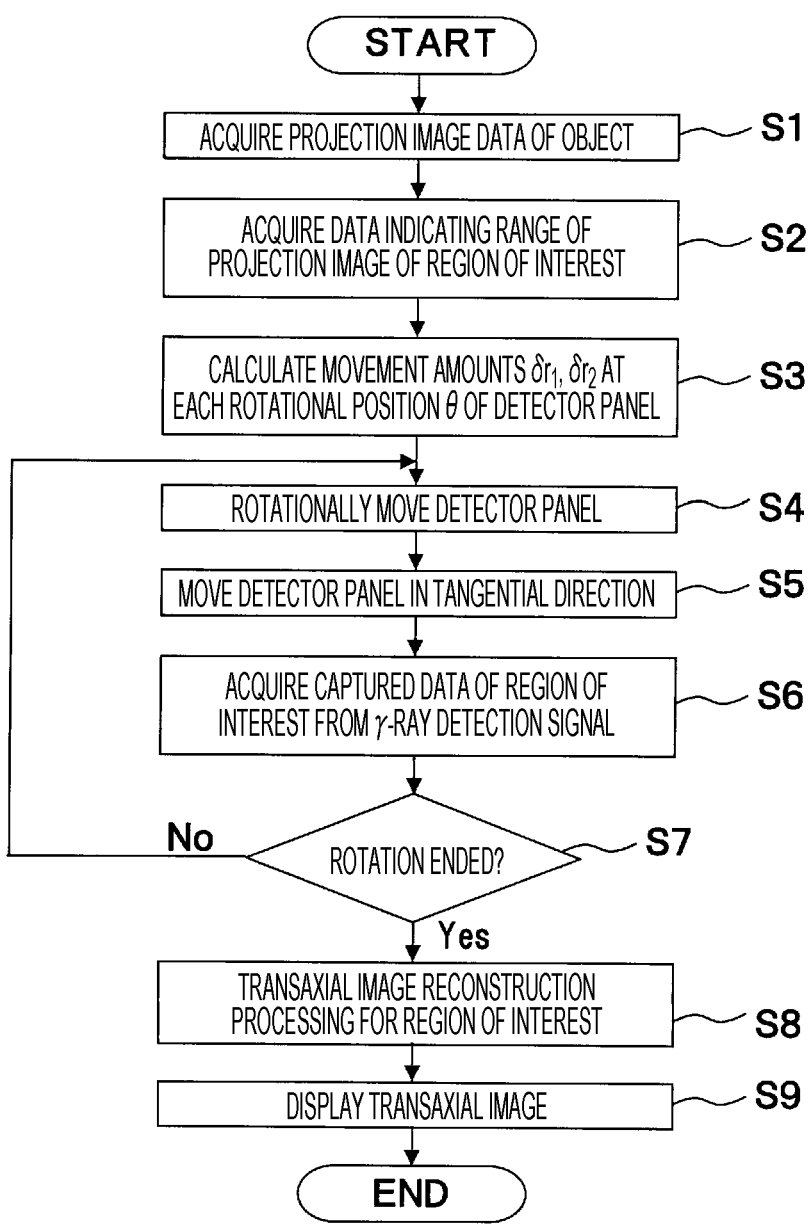
FIG. 8 is a diagram illustrating a procedure for acquiring a transaxial image of the region of interest by the SPECT system according to the embodiment of the present invention.

FIG. 8 is a diagram illustrating the procedure for acquiring a transaxial image of the region of interest 31 by the SPECT system 1 according to this embodiment of the present invention. This procedure summarizes the method of acquiring a transaxial image of the region of interest 31 that has been illustrated thus far.

Firstly, using, inter alia, an X-ray CT apparatus, projection image data of the object 15 containing the region of interest 31 is acquired (step S1). Projection image data refers to a type of data in, e.g., a sinogram form (see FIGS. 4(a) to 4(d)) and stored in a storage device of the data processing device 12. The X-ray CT apparatus may be of a different type from that of the SPECT system 1 or of a type of apparatus attached to the SPECT system 1 when the SPECT system 1 is a SPECT-CT apparatus.

The data processing device 12 uses projection image data of the object 15 and thereby acquires data representing the range of the projection image of the region of interest 31 (ROI($θ_a$) as referred to in FIG. 2, etc.) (step S2). Also, the movement amounts $δr_1, δr_2$ in the tangential direction r during rotation are calculated for each rotational position θ of the detector panels $d_1, d_2$ (step S3).

The gantry 10 rotationally moves the detector panels $d_1, d_2$ at a predetermined unit angle (e.g., a unit of 10 degrees) (step S4), and the detector panels $d_1, d_2$ are moved in the tangential direction r (step S5). The rotational movement of the detector panels $d_1, d_2$ and the movement thereof in the tangential direction r may take place simultaneously. The movement in the tangential direction r may take place after the rotational movement ends.

In turn, the detector panels $d_1, d_2$ acquires captured data of the region of interest 31 from a detection signal whereby a gamma ray has been detected (step S6). This captured data is, e.g., an equivalent of projection image data in a sinogram form at the rotational position θ and is sent to the data processing device 12.

A control device that controls the gantry 10, etc. determines whether the rotational movement of the detector panels $d_1, d_2$ should be ended (step S7). Normally, the rotational movement is determined to have been ended when the detector panels $d_1, d_2$ have rotated 360 degrees. When the rotational movement is not determined to have been ended ("No" in step S7), the procedure goes back to step S4, and step S4 and the steps subsequent thereto are performed again.

When determined to have been ended in step S7 ("Yes" in step S7), the data processing device 12 executes reconstruction processing for a transaxial image of the region of interest 31 (step S8). The transaxial image of the reconstructed region of interest 31 is displayed on, e.g., the display device 13 (step S9). Reconstruction processing for the transaxial image of the region of interest 31 may employ the MLEM method, the OSEM method, and other publicly known successive approximation reconstruction methods.

As described above, according to the first embodiment of the present invention, even when the capturing range (FOV) of the detector panel 11 is shorter than the length of ROI(θ) of the region of interest 31 in the tangential direction r, the two detector panels 11($d_1, d_2$) can be used to move the capturing range (FOV) to the positions where the ROI(θ) that is calculated for each rotational position θ is maximum and minimum. Thereby, a transaxial image of the region of interest 31 can be acquired, and the image quality thereof can be enhanced.

In an additional note, as a gamma ray detector of the detector panel 11, use of a semiconductor detector is more desirable than use of a scintillation detector. A semiconductor detector is superior to a scintillation detector in terms of characteristic spatial resolution and energy resolution. As a scintillation detector uses a high-electron photomultiplier tube, the size of the detector panel 11 increases, whereby the total weight, including the weight of a radiation shielding material, increases. A semiconductor detector is more compact than the scintillation detector, and the former is smaller than the latter in terms of weight. According to this embodiment, as a mechanism for moving the detector panel 11 in the tangential direction r is additionally provided, a lightweight and compact semiconductor detector is suitable.

Modified Embodiment of the First Embodiment

Figure 9:
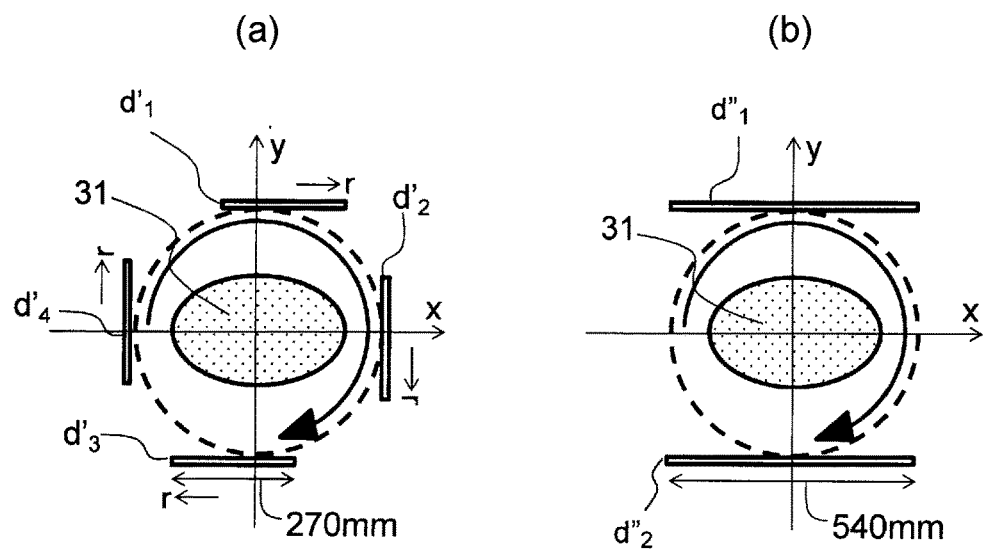
FIGS. 9(a) and 9(b) represent diagrams illustrating a modified embodiment of a first embodiment.

FIGS. 9(a) and 9(b) represent diagrams illustrating a modified embodiment of the first embodiment. FIG. 9(a) is a diagram illustrating an example situation of a gamma ray projection image using four small-area detector panels according to the modified embodiment of the first embodiment. FIG. 9(b) is a diagram illustrating an example situation of a gamma ray projection image using two large-area detector panels according to a comparative embodiment.

According to the first embodiment, the above-described example is where a gamma ray projection image of the region of interest 31 is acquired using the two small-area detector panels $d_1, d_2$. However, the number of the used detector panels 11 not limited to two and may be three or more. In the below-illustrated examples, the four detector panels 11 are used.

As illustrated in FIG. 9(a), when four detector panels $d'_1, d'_2, d'_3, d'_4$ are used, for each of the two detector panels ($d'_1, d'_3$) and the two detector panels ($d'_2, d'_4$) that are opposite to each other, movement amounts $δr'_1, δr'_3, δr'_2, δr'_4$, respectively, which are equivalents of the movement amounts illustrated in the first embodiment, are calculated. The detector panels $d'_1, d'_3$ are moved to the positive tangential direction r, and the detector panels $d'_2, d'_4$ are moved to the negative tangential direction r. In this case, the lengths of the four detector panels $d'_1, d'_2, d'_3, d'_4$ in the tangential direction r are all shorter than the maximum length of the region of interest 31 and are assumed to be, e.g., 270 mm.

In this modified embodiment, the time taken for rotational movement of the detector panels $d'_1, d'_2, d'_3, d'_4$ for acquiring a projection image of the region of interest 31 can be half as long as the time taken in the case of using the two detector panels $d_1, d_2$ (first embodiment). To acquire a projection image for 360 degrees of the region of interest 31, the detector panels $d'_1, d'_2, d'_3, d'_4$ need to be rotated only 180 degrees. Specifically, the detector panels $d'_1, d'_3$ need to be rotated between 0 and 180 degrees and between 180 and 360 degrees, and the detector panels $d'_2, d'_4$ need to be rotated between 90 and 270 degrees and between 270 and 90 degrees.

Also, in this modified example, the accuracy of the projection image of the region of interest 31 by rotating the detector panels $d'_1, d'_2, d'_3, d'_4$ 360 degrees is higher than the accuracy when using the two detector panels $d_1, d_2$ (first embodiment). As a result, the quality of a transaxial image of the region of interest 31 can be enhanced due to an increase in the number of gamma ray counts per pixel of the projection image of the region of interest 31.

The comparative embodiment of FIG. 9(b) uses the two detector panels $d''_1, d''_2$, and the length in tangential direction r is approximately 540 mm. Such a configuration of the detector panels $d''_1, d''_2$ is commonly employed in the conventional SPECT system for the entire body. Also, the total area on the gamma ray incident side of the detector panels $d''_1, d''_2$ employed in this comparative embodiment is approximately equal to that of the example of FIG. 9(a).

Figure 10:
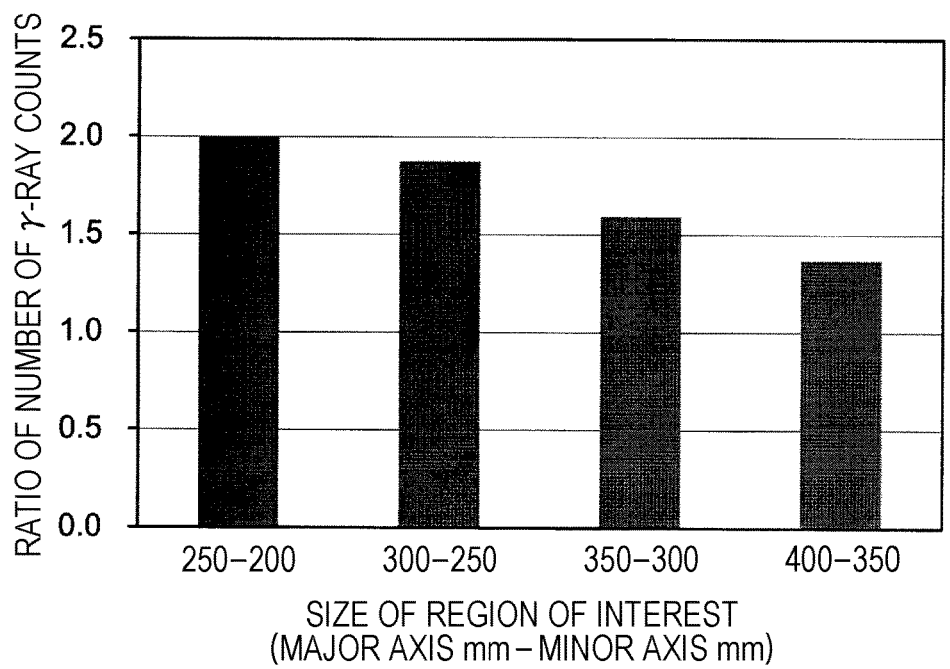
FIG. 10 is a diagram illustrating example simulation results of the ratio of the number of gamma ray counts with respect to the size of the region of interest when four small-area detector panels are used and when two large-area detection panels are used.

FIG. 10 is a diagram illustrating example simulation results of the ratio of the number of gamma ray counts with respect to the size of the region of interest 31 when four small-area detector panels are used (see FIG. 9(a)) and when two large-area detection panels are used (see the comparative embodiment of FIG. 9(b)). It is assumed here that the size and shape of the region of interest 31 is an ellipse with a major diameter (mm) and a minor diameter (mm).

As illustrated in FIG. 10, when the region of interest 31 (with a major diameter of 250 mm and a minor diameter of 200 mm) is shorter than the length (270 mm) of the small-area detector panels $d'_1, d'_2, d'_3, d'_4$ in the tangential direction r, the ratio of the number of counts is obviously twice larger. When the major diameter of the region of interest 31 exceeds the length (270 mm) of the detector panels $d'_1, d'_2, d'_3, d'_4$ in the tangential direction r, the ratio of the number of counts gradually decreases from 2. However, even when the size of the region of interest 31 increases to a significant extent (e.g., when the major diameter is 400 mm and the minor diameter is 350 mm), the ratio of the number of counts is approximately 1.4.

Accordingly, compared with the comparative embodiment where the conventional two large-area detection panels $d''_1, d''_2$ are used (see FIG. 4(b)), the accuracy of a gamma ray projection image of the region of interest 31—in other words, the quality of a transaxial image of the region of interest 31—is enhanced in this modified embodiment (see FIG. 9(a)). When the image quality of the region of interest 31 does not need to be enhanced, the time for capturing a gamma ray projection image of the region of interest 31 can be shortened. As a result, the dose of a radioactive drug to the object 15 and the radiation exposure of the object 15 can be decreased.

Second Embodiment

According to the first embodiment, the detector panels $d_1, d_2$ are moved at each rotational position θ of the detector panels $d_1, d_2$ in the tangential direction r. According to a second embodiment, the detector panels $d_1, d_2$ are assumed not to be moved in the tangential direction r during rotation of the detector panels $d_1, d_2$. In this case, prior to starting capture of a projection image of the region of interest 31, the detector panels $d_1, d_2$ are in advance moved in the tangential direction r.

Figure 11:
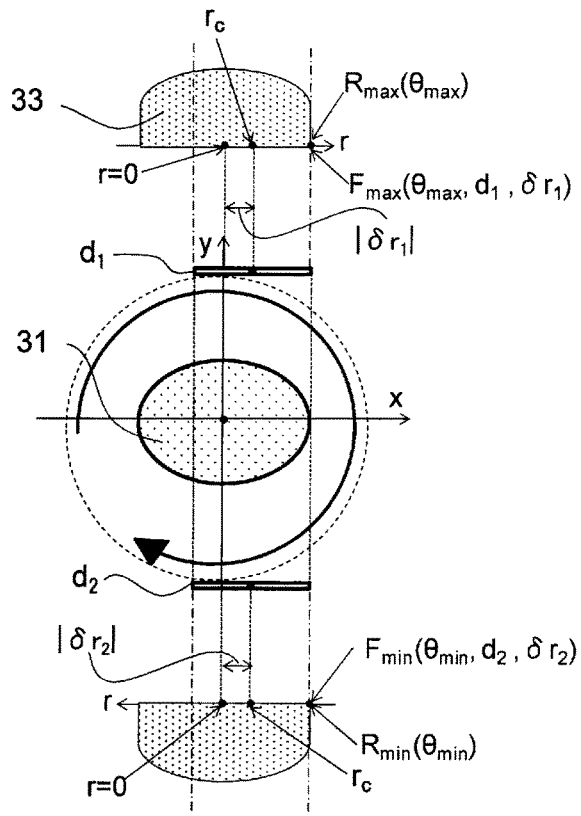
FIG. 11 is a diagram illustrating an example situation of acquiring a gamma ray projection image using two detector panels according to a second embodiment of the present invention.

FIG. 11 is a diagram illustrating an example situation of acquiring a projection image using the two detector panels $d_1, d_2$ according to the second embodiment of the present invention. As in the case of the first embodiment, it is assumed in the second embodiment that the length of the capturing range of the detector panels $d_1, d_2$ in the tangential direction r is eventually shorter than the length of the region of interest 31. The positions where the size of the projection image 33 of the region of interest 31 at the rotational position θ is maximum and maximum in the tangential direction r are denoted by $R_{min}(\theta)$ and $R_{max}(\theta)$, respectively. The maximum value of $R_{max}(\theta)$ and the minimum value of $R_{min}(\theta)$ are denoted by $R_{max}(\theta_{max})$ and $R_{min}(\theta_{min})$, respectively, and the respective rotational positions θ are denoted by $\theta_{max}$ and $\theta_{min}$.

In this case, as illustrated in FIG. 11, in order for $F_{max}(\theta_1, d_1, \delta r_1)$ where the capturing range of the detector panel $d_1$ at the rotational position $\theta_{max}$ is maximum in the tangential direction r, to be positioned near $R_{max}(\theta_{max})$, the center position $r_c$ of the detector panel $d_1$ is moved from the center (r=0) by $\delta r_1$ in the tangential direction r. Also, in order for $F_{min}(\theta_{min}, d_2, \delta r_2)$, where the capturing range of the detector panels $d_2$ at the rotational position $\theta_{min}$ is minimum in the tangential direction r, to be positioned near $R_{min}(\theta_{min})$, the center position $r_c$ of the detector panel $d_2$ is moved from the center (r=0) by $\delta r_2$ in the tangential direction r.

It is assumed here that the sum of the capturing ranges of the two detector panels $d_1, d_2$ in the tangential direction r, $(L(d_1)+L(d_2))$, is longer than $|R_{max}(\theta_{max})-R_{min}(\theta_{min})|$.

As can be seen in the above, in order to conduct SPECT image capturing (gamma ray projection image capturing), the detector panels $d_1, d_2$ are moved by $\delta r_1, \delta r_2$, respectively, in the tangential direction r, and then SPECT image capturing is started. In this case, SPECT image capturing can be performed only by rotating the detector panels $d_1, d_2$. As the detector panels $d_1, d_2$ do not need to be moved in the tangential direction r, control processing for moving the detector panels $d_1, d_2$ can be simplified. When there is an overlapping portion in the capturing ranges of the two detector panels $d_1, d_2$, the accuracy of a gamma ray projection image and the quality of a transaxial image is higher than the accuracy and quality when using one large-area detector panel.

Figure 12:
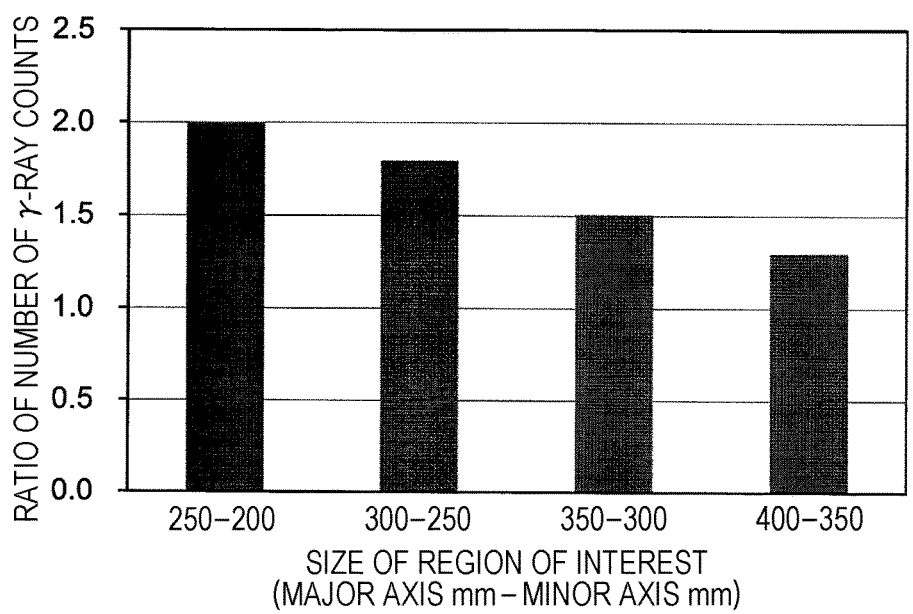
FIG. 12 is a diagram illustrating example simulation results of the ratio of the number of gamma ray counts with respect to the region of interest by applying the second embodiment to the situation where four small-area detector panels are used and to the situation where two large-area detection panels are used.

FIG. 12 is a diagram illustrating example simulation results of the ratio of the number of gamma ray counts with respect to the size of the region of interest 31 by applying the second embodiment to the situation where four small-area detector panels are used (see FIG. 9(a)) and to the situation where two large-area detection panels are used (see the comparative embodiment of FIG. 9(b)). Here, as illustrated in FIGS. 9(a) and 9(b), the length of the small-area detector panel in the tangential direction r is 270 mm, and the length of the large-area detector panel in the tangential direction r is 540 mm.

As illustrated in FIG. 12, when the region of interest 31 is shorter than the length (270 mm) of the small-area detector panel (with a major diameter of 250 mm and a minor diameter of 200 mm) in the tangential direction r, the ratio of the number of counts is obviously twice larger. When the major diameter of the region of interest 31 exceeds the length (270 mm) of the detector panel in the tangential direction r, the ratio of the number of counts gradually decreases from 2. However, even when the region of interest 31 increases to a significant extent (e.g., when the major diameter is 400 mm and the minor diameter is 350 mm), the ratio of the number of counts is approximately 1.3. A decrease in the ratio of the number of counts is greater than that of FIG. 10 (modified embodiment of the first embodiment).

As described above, compared with the embodiment where one or two conventional large-area detection panels are used, the accuracy of a gamma ray projection image of the region of interest 31—in other words, the quality of a transaxial image of the region of interest 31—is enhanced according to the second embodiment. When the image quality of the region of interest 31 does not need to be enhanced, the time for capturing a gamma ray projection image of the region of interest 31 can be shortened. As a result, the dose of a radioactive drug to the object 15 and the radiation exposure of the object 15 can be decreased.

Third Embodiment

Figure 13:
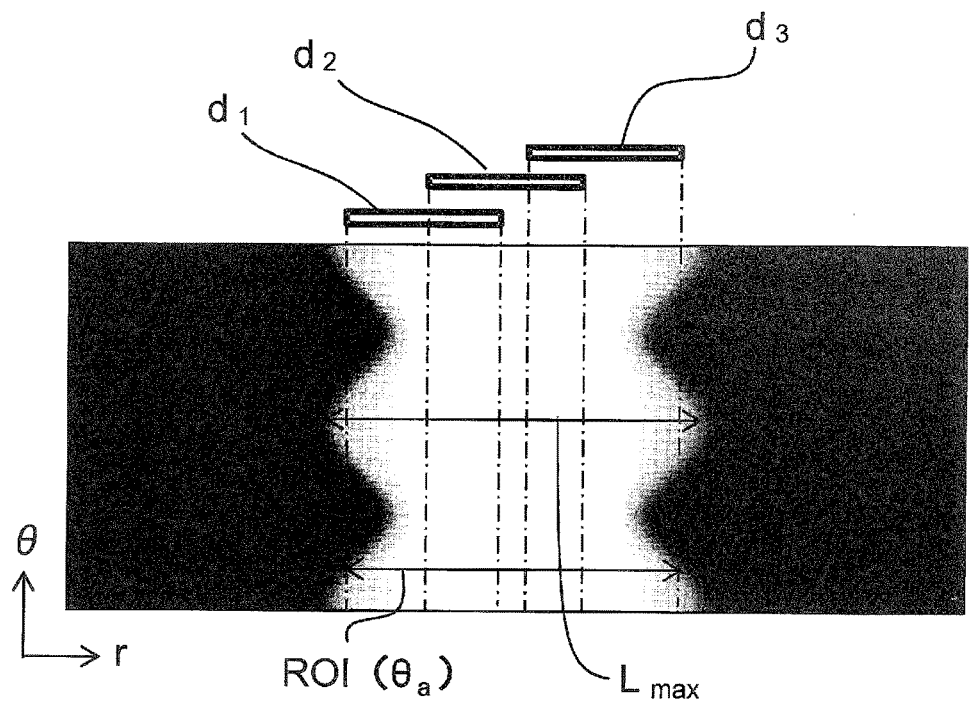
FIG. 13 is a diagram illustrating an example situation of overlapping of capturing ranges when three small-area detector panels $d_1, d_2, d_3$ are used according to a third embodiment of the present invention.

FIG. 13 is a diagram illustrating an example situation where the capturing ranges are overlapped when the three small-area detector panels $d_1, d_2, d_3$ are used according to a third embodiment of the present invention. According to the first and second embodiments, the range $ROI(\theta_a)$ of a projection image of the region of interest 31 is captured by the two detector panels $d_1, d_2$ without causing a truncation error. However, the number of detectors capturing $ROI(\theta_a)$ may be three or more.

For example, as illustrated in FIG. 13, the range $ROI(\theta_a)$ of the projection image of the region of interest may be contained in union $FOV(\theta_a, d_1, \delta r_1) \cup FOV(\theta_a, d_2, \delta r_2) \cup FOV(\theta_a, d_3, \delta r_3)$ of the capturing ranges of the three detector panels $d_1, d_2, d_3$, where: $L_{max}$ denotes the maximum value of the length of $ROI(\theta)(=|R_{max}(\theta) - R_{min}(\theta)|)$, which is the range of the region of interest 31; $L(d_i)$ denotes the length of the capturing range of the detector panel $d_i$ in the tangential direction r; and N denotes the number of used detector panels. In this case, to conduct capturing during one rotational movement of the detector panels $d_1, d_2, d_3$ in the configuration of the first embodiment without causing a truncation error, $L(d_i)$ needs to be set so as to satisfy the following equation:

[Formula 1]

$$\Sigma_{i=1}^{N} L(d_i) \geq L_{max} \quad (4)$$

Also, the maximum value of $R_{max}(\theta)$ and the minimum value of $R_{min}(\theta)$, both of which are dependent on the rotational position $\theta$ are denoted by $R_{max}(\theta_{max})$ and $R_{min}(\theta_{min})$, respectively. The respective rotational positions $\theta$ are denoted by $\theta_{max}$ and $\theta_{min}$, and $|R_{max}(\theta_{max}) - R_{min}(\theta_{min})|$ is denoted by $L'_{max}$. In this case, to conduct capturing during one rotational movement of the detector panels $d_1, d_2, d_3$ in the configuration of the second embodiment without causing a truncation error, $L(d_1)$ needs to be set so as to satisfy the following equation:

[Formula 2]

$$\Sigma_{i=1}^{N} L(d_i) \geq L'_{max} \quad (5)$$

As described above, as in the case of the third embodiment, an advantageous effect of using a plurality of small-area detector panels $d_i$ is, e.g., significant enhancement of the quality of a transaxial image by focusing a plurality of the detector panels $d_i$ on the region of interest 31 when the capturing target is, e.g., the heart, and the size of the region of interest 31 of the capturing target is small.

Fourth Embodiment

Figure 14:
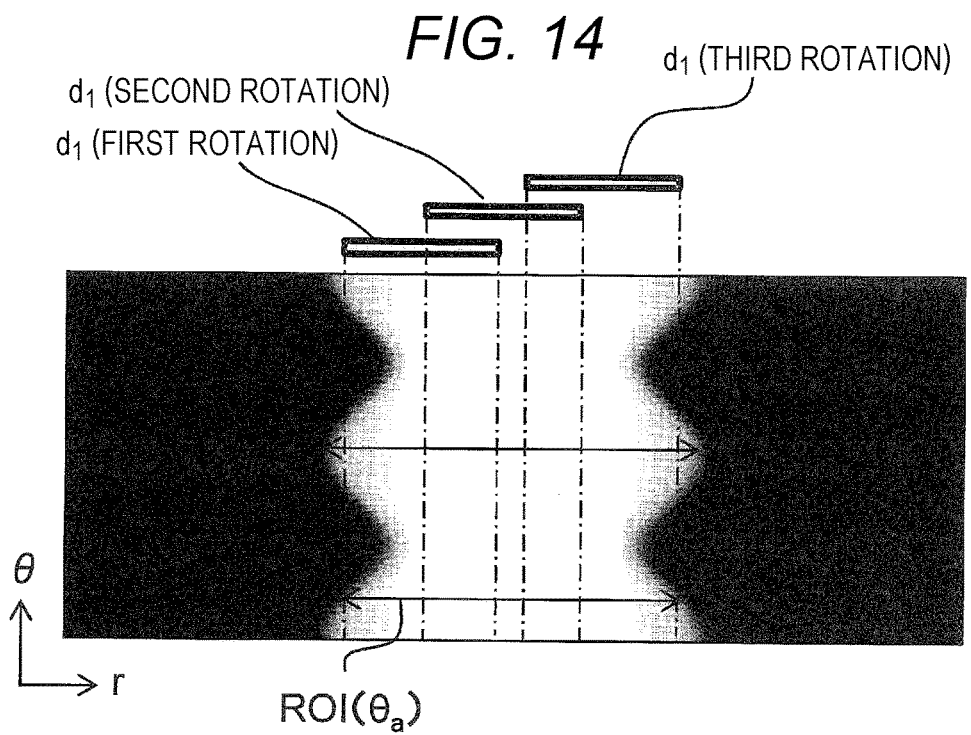
FIG. 14 is a diagram illustrating an example situation of overlapping of capturing ranges during a plurality of rotational movements of one small-area detector panel $d_1$ according to a fourth embodiment of the present invention.

FIG. 14 is a diagram illustrating an example situation of overlapping of capturing ranges during a plurality of rotational movements of one small-area detector panel $d_1$ according to a fourth embodiment of the present invention. In the above-illustrated embodiments, methods of capturing the region of interest 31 by one rotational movement (360 degrees) of a plurality of the small-area detector panels 11 without causing a truncation error are illustrated. However, the region of interest 31 can be captured by a plurality of rotational movements of one small-area detector panel 11 without causing a truncation error.

As illustrated in FIG. 14, there can be an example situation where the range $ROI(\theta_a)$ of the projection image of the region of interest 31 is twice as long as the length $L(d_1)$ of the detector panel $d_1$ in the tangential direction r. Even in such a situation, by moving the detector panel $d_1$ in the tangential direction r and repeating a 360-degree rotational movement three times, the region of interest 31 can be captured by one detector panel $d_1$ without causing a truncation error.

Fifth Embodiment

In this embodiment, the situation where the length of a diagnosis target in tangential direction r is shorter than the length of the capturing range of the detector panel 11 in the tangential direction r is illustrated. For example, when a human head is a capturing target, the length (e.g., 270 mm) of the capturing range of the detector panel 11 in the tangential direction r is often longer than the length of the human head in many cases. In such a case, capturing can be performed without moving the detector panel 11 in the tangential direction r.

Figure 15:
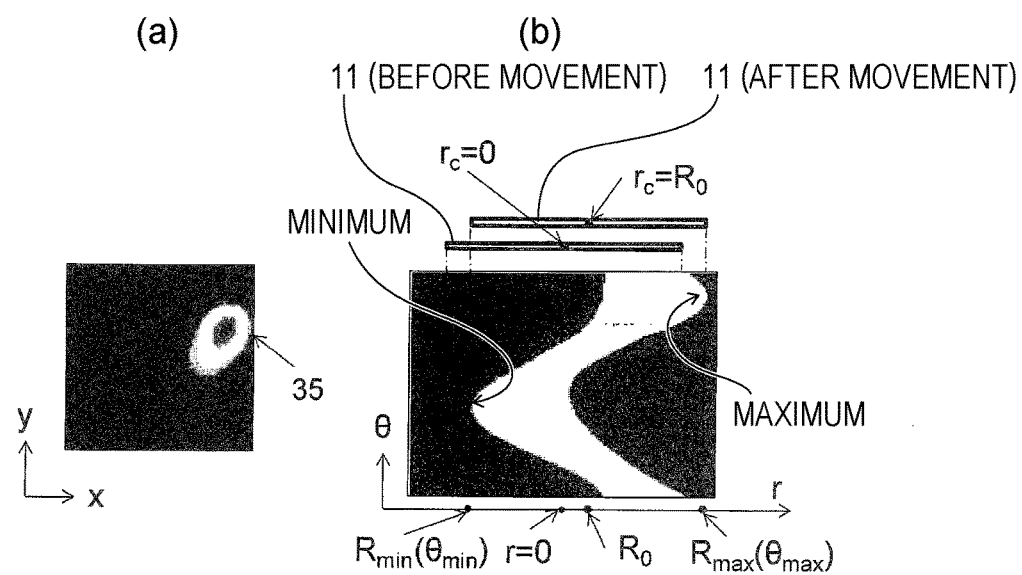
FIGS. 15(a) and 15(b) represent diagrams illustrating examples where the region of the heart, which is the region of interest, is deviated from the center of the image.

FIGS. 15(a) and 15(b) represent diagrams illustrating examples where the region of the heart 35, which is the region of interest 31, is deviated from the center of the image. FIG. 15(a) illustrates an example transaxial image, and FIG. 15(b) illustrates an example projection image. In the situation of FIGS. 15(a) and 15(b) where the heart 35, which is the region of interest 31, is deviated from the center of the image, even when the size of the region of interest 31 is shorter than the length of the capturing range of the detector panel 11 in the tangential direction r, the region of interest 31 at a certain rotational position is not eventually contained in the capturing range of the detector panel 11.

Here, the positions where the size of the projection image of the region of interest 31 at the rotational position $\theta$ is maximum and maximum in the tangential direction r are denoted by $R_{min}(\theta)$ and $R_{max}(\theta)$, respectively. The maximum value of $R_{max}(\theta)$ and the minimum value of $R_{min}(\theta)$ are denoted by $R_{max}(\theta_{max})$ and $R_{min}(\theta_{min})$, respectively. The respective rotational positions $\theta$ are denoted by $\theta_{max}$ and $\theta_{min}$.

In this case, when $(R_{max}(\theta_{max}) + R_{min}(\theta_{min}))/2$ is assumed to be denoted by $R_0$, as illustrated in FIG. 15(b), by moving the center position $r_c$ of the detector panel 11 to $R_0$, the region of interest 31 can be covered at all the rotational positions. However, the length of the capturing range of the detector panel 11 in the tangential direction r is assumed to be longer than $|R_{max}(\theta_{max}) - R_{min}(\theta_{min})|$. Accordingly, prior to capturing the object, by moving the center position of the detector panel 11 to the position $R_0$ in the tangential direction r and fixing the position of the detector panel 11 in the tangential direction r for capturing, projection image data without a truncation error can be acquired.

Figure 16:
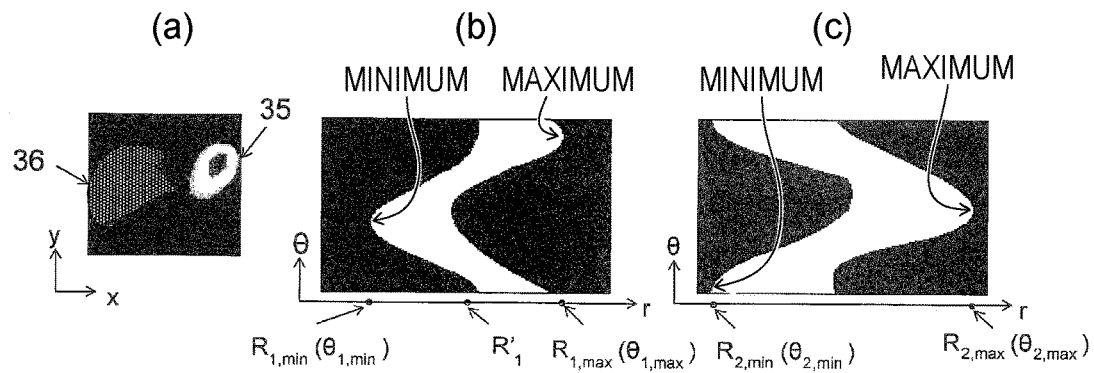
FIGS. 16(a) to 16(c) represent diagrams illustrating examples where the heart and the liver, which is the region of interest and is not the region of interest, respectively, are contained in the same transaxial image.

FIGS. 16(a) to 16(c) represent diagrams illustrating examples where the heart 35 and the liver 36, which is the region of interest 31 and is not the region of interest 31, respectively, are contained in the same transaxial image. FIG. 16(a) illustrates an example transaxial image containing the heart 35 and the liver 36; FIG. 16(b) illustrates an example projection image that can be acquired from a transaxial image of the heart 35; and FIG. 16(c) illustrates an example projection image that can be acquired from a transaxial image of the liver 36.

As illustrated in FIG. 16(a), when the heart 35 is the region of interest 31, the liver 36, which is not the region of interest 31, can be contained in the same transaxial image. In such a case, capturing can be performed by focusing the detector panel 11 on the heart 35. However, in an event that a gamma ray originated from a medical agent that can be accumulated in the liver 36 depending on the rotational position θ of the detector panel 11 is detected, gamma ray detection from an image of the heart 35 is less reliable on a quantitative basis. The text to follow illustrates a method of restraining a decrease in the reliability of gamma ray detection on a quantitative basis with presence of radioactive drug distribution of an internal organ that is not the region of interest 31 and can cause background noise near the region of interest 31 where a radioactive drug is distributed.

As illustrated in FIG. 16(b), $R_{max}(\theta)$ and $R_{min}(\theta)$ of the heart region at the rotational position θ are denoted by $R_{1,max}(\theta)$ and $R_{1,min}(\theta)$, respectively. The maximum value of $R_{1,max}(\theta)$ and the minimum value of $R_{1,min}(\theta)$ are denoted by $R_{1,max}(\theta_{1,max})$ and $R_{1,min}(\theta_{1,min})$, respectively. The corresponding rotational positions θ are denoted by $\theta_{1,max}$ and $\theta_{1,min}$.

As illustrated in FIG. 16(c), $R_{max}(\theta)$ and $R_{min}(\theta)$ of the liver region at the rotational position θ are denoted by $R_{2,max}(\theta)$ and $R_{2,min}(\theta)$, respectively. The maximum value of $R_{2,max}(\theta)$ and the minimum value of $R_{2,min}(\theta)$ are denoted by $R_{2,max}(\theta_{2,max})$ and $R_{2,min}(\theta_{2,min})$, respectively. The corresponding rotational positions θ are denoted by $\theta_{2,max}$ and $\theta_{2,min}$.

Also, whichever is the larger of $R_{1,max}(\theta_{1,max})$ and $R_{2,max}(\theta_{2,max})$ is denoted by $R_{max}$, and whichever is the smaller of $R_{1,min}(\theta_{1,min})$ and $R_{2,min}(\theta_{2,min})$ is denoted by $R_{min}$. In this case, when the length of the capturing range of the detector panel 11 is longer than $|R_{max}-R_{min}|$, by moving the center position $r_c$ of the detector panel 11 to the position of $(R_{max}+R_{min})/2$ prior to capturing and fixing the position of the detector panel 11 in the tangential direction r for capturing, projection image data without a truncation error can be acquired. The foregoing capturing method is an equivalent of setting both the heart 35 and the liver 36 as the region of interest 31 in the capturing method of FIGS. 15(a) and 15(b) where the heart 35 is the region of interest 31.

Also, the text to follow addresses the situation where the capturing range contains the heart 35 in whole and the liver 36 in part even when the detector panel 11 is moved in the tangential direction r. In this situation, the detector panel is moved in the tangential direction r so that the heart 35 is contained in the capturing range and the area where the liver 36 is contained is maximum. $(R_{1,min}(\theta)+R_{1,max}(\theta))/2$ of the heart region at the rotational position θ is denoted by $R_1(\theta)$.

Here, the length L(d) of the capturing range of the detector panel 11 in the tangential direction r is assumed to be longer than $|R_{1,max}(\theta)-R_{1,min}(\theta)|$, and $(L(d)-|R_{1,max}(\theta)-R_{1,min}(\theta)|)$ is denoted by $\Delta L(\theta)$. In this case, when the center position $r_c$ of the detector panel 11 is in the range of $[R_1(\theta)-\Delta L(\theta)/2, R_1(\theta)+\Delta L(\theta)/2]$, a truncation error relating to the heart region does not occur.

In this range, $r_{c,max}(\theta)$ denotes the position where the number of gamma ray counts $Ct(r_c)$, which is detected from the liver region when the center position $r_c$ of the detector panel is moved, is maximum. The position $r_{c,max}(\theta)$ is calculated from projection image data $Pj(r,\theta)$ of the liver region of FIG. 16(c). Specifically, the center position $r_c$ of the detector panel 11 is changed in the range of $[R_1(\theta)-\Delta L(\theta)/2, R_1(\theta)+\Delta L(\theta)/2]$; the number of counts $Ct(r_c)$, which can be acquired from projection data of the liver region within the capturing range of $[r_c-L(d)/2, r_c+L(d)/2]$ is calculated by following equation (6); and the position $r_{c,max}(\theta)$ where the number of counts is maximum is calculated:

[Formula 3]

$$Ct(r_c)=\Sigma_{r=r_c-L(d)/2}^{r=c+L(d)/2} Pj(r,\theta) \qquad (6)$$

By performing capture while the center position of the detector panel 11 is moved to the position $r_{c,max}(\theta)$ at each rotational position θ, a decrease in the reliability of gamma ray detection on a quantitative basis due to the background noise of the liver can be restrained. As described above, a capturing method for the situation where the capturing range contains the heart 35 in whole and the liver 36 in part requires that the detector panel be moved at each rotational position θ in the tangential direction r.

The text to follow illustrates a capturing method for the situation where the detector panel 11 is moved only once in the tangential direction r prior to capturing.

As illustrated in FIG. 16(b), the maximum value of $R_{1,max}(\theta)$ and the minimum value of $R_{1,min}(\theta)$ in the heart region are denoted by $R_{1,max}(\theta_{1,max})$ and $R_{1,min}(\theta_{1,min})$, respectively, and $(R_{1,max}(\theta_{1,max})+R_{1,min}(\theta_{1,min}))/2$ is denoted by $R'_1$. Also, the length of the capturing range of the detector panel 11 in the tangential direction r is demoted by L(d). L(d) is assumed to be longer than $|R_{1,max}(\theta_{1,max})-R_{1,min}(\theta_{1,min})|$, and $(L(d)-|R_{1,max}(\theta_{1,max})-R_{1,min}(\theta_{1,min})|)$ is denoted by $\Delta L'$.

In this case, when the center position $r_c$ of the detector panel 11 is in the range of $|R'_1-\Delta L'/2, R'_1+\Delta L'/2|$, a truncation error relating to the heart region does not occur. $r'_{c,max}$ denotes the position where the number of gamma ray counts $Ct(r_c)$ detected from the liver region is maximum when the center position $r_c$ of the detector panel is moved in this range. $r'_{c,max}$ is calculated from projection image data $Pj(r,\theta)$ of the liver region of FIG. 16(c). Specifically, the center position $r_c$ of the detector panel 11 is changed in the range of $[R'_1-\Delta L'/2, R'_1+\Delta L'/2]$; the number of counts $Ct(r_c)$, which can be acquired from projection data of the liver region in the capturing range of $[r_c-L(d)/2, r_c+L(d)/2]$ is calculated by following equation (7); and the position $r'_{c,max}$ where the number of counts is maximum is calculated:

[Formula 4]

$$Ct(r_c)=\Sigma_{r=r_c-L(d)/2}^{r=r_c+L(d)/2}\Sigma_{\theta=0}^{\theta=360} Pj(r,\theta) \qquad (7)$$

In this case, by moving the center position of the detector panel 11 to the position $r'_{c,max}$ prior to capturing, capturing can be performed while the position of detector panel 11 is fixed in the tangential direction r. A decrease in the reliability of gamma ray detection on a quantitative basis due to the background noise of the liver 36 can be restrained. The above-illustrated method according to this embodiment is not limited to a system using one detector panel 11 and is applicable for a system using a plurality of the detector panels 11.

Sixth Embodiment

According to the fifth embodiment, only the heart is the region of interest 31, and the liver is background. However, a transaxial image may be reconstructed by setting both the heart and the liver as the region of interest 31 and acquiring projection image data by the methods of the first to fourth embodiments.

Seventh Embodiment

Figure 17:
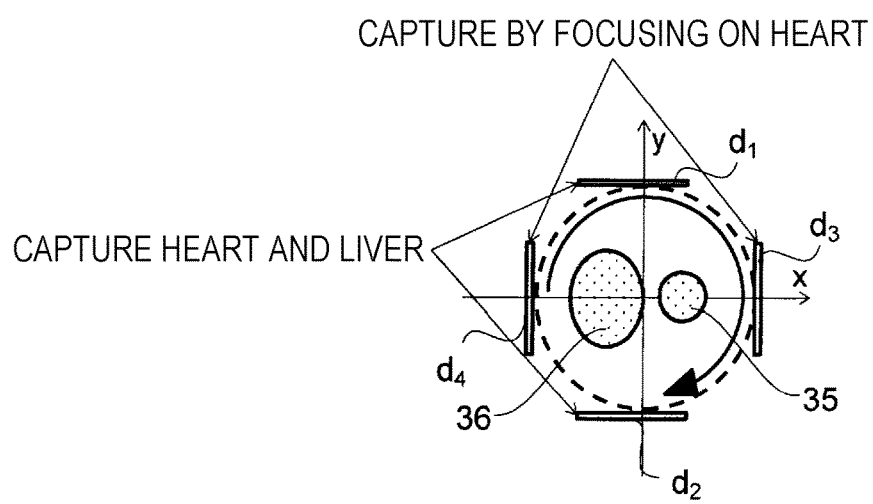
FIG. 17 is a diagram illustrating an example where the detector panels $d_3, d_4$ focused only on the heart region are added to ensure the reliability of gamma ray detection on a quantitative basis in the heart region.

FIG. 17 is a diagram illustrating an example where the detector panels $d_3,d_4$ focused only on the heart region are added to ensure the reliability of gamma ray detection on a quantitative basis in the heart region. Within the context of the first to sixth embodiments, by adding the detector panels $d_3,d_4$ focused only on the heart, which is the region of interest 31, the reliability of γ-ray detection on a quantitative basis in the heart region can be ensured while enhancing the γ-ray detection sensitivity of the heart region.

For example, in the system illustrated in FIG. 17 where the four detector panels $d_1,d_2,d_3,d_4$ are used, capturing is performed by the detector panels $d_1,d_2$ by setting both the heart and liver as the region of interest in the methods of the first to sixth embodiments. Also, capturing is performed by focusing only on the heart by the detector panels $d_3,d_4$.

Accordingly, capturing data acquired by combined use of the detector panels $d_1,d_2$ is data that does not contain a truncation error relating to the heart or liver. Also, capturing data acquired by the detector panels $d_3,d_4$ is data that does not contain a truncation error relating to the heart. However, the capturing data acquired by the detector panels $d_3,d_4$ may contain a truncation error relating to the liver. By combining all the above types of data, occurrence of a truncation error relating to both the heart and liver can be avoided, and the gamma ray detection sensitivity of the heart region can be enhanced.

Eighth Embodiment

Figure 18:
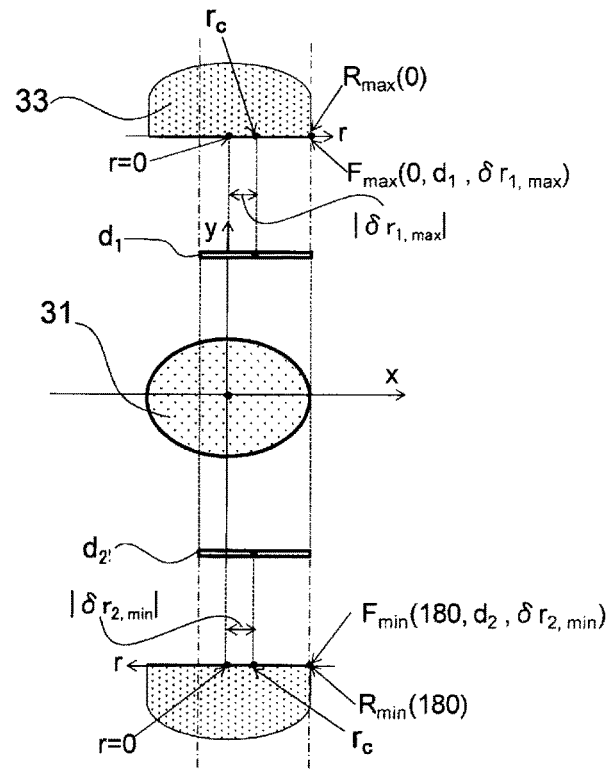
FIGS. 18(a) and 18(b) are diagrams illustrating examples of planar image capturing of the region of interest.
Figure 18:
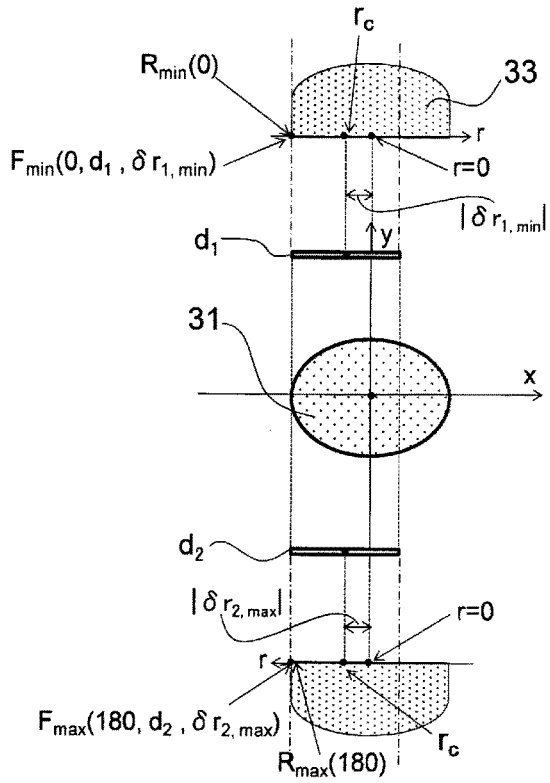

FIGS. 18(a) and 18(b) represent diagrams illustrating examples of planar image capturing of a region of interest. FIG. 18(a) is a diagram illustrating that the two detector panels $d_1,d_2$ are moved, respectively, to the position where the region of interest is maximum in the positive direction and to the position where the region of interest is minimum in the negative direction. FIG. 18(b) is a diagram illustrating that the two detector panels $d_1,d_2$ are moved, respectively, to the position where the region of interest is minimum in the negative direction and to the position where the region of interest is maximum in the positive direction. In the technique according to the above-illustrated embodiments, information on the range of a projection image in the region of interest 31 is used to efficiently arrange the detector panel 11 for enhancing the quality of a captured SPECT transaxial image. This technology is applicable for planar image capturing of the region of interest 31. Planar image capturing of the region of interest 31 is hereinafter illustrated by referring to FIGS. 18(a) and 18(b).

In this embodiment, planar image capturing using the two detector panels $d_1,d_2$ is illustrated. Here, the detector panels $d_1,d_2$ are disposed at positions where the rotational positions θ are 0 degree and 180 degrees, respectively. Both of the lengths of the capturing range in the tangential direction r, $L(d_1)$ and $L(d_2)$, are assumed to be shorter than the length of the projection image of the region of interest 31 in the tangential direction r. By efficiently moving the detector panel in the tangential direction as in the case of transaxial image capturing, the region of interest 31 is captured.

Firstly, based on projection image data acquired from, e.g., an X-ray CT apparatus, positional information ($R_{min}(0),R_{max}(0),R_{min}(180),R_{max}(180)$) of the end portion of a projection image of the region of interest 31 is acquired. The movement amounts $\delta r_{1,max}, \delta r_{1,min}, \delta r_{2,max}, \delta r_{2,min}$ of the detector panels $d_1,d_2$ illustrated in FIG. 18(a) and FIG. 18(b) are calculated by equations (8) to (11):

$$\delta r_{1,max}=R_{max}(0)-L(d_1)/2 \tag{8}$$

$$\delta r_{1,min}=R_{min}(0)+L(d_1)/2 \tag{9}$$

$$\delta r_{2,max}=R_{max}(180)-L(d_2)/2 \tag{10}$$

$$\delta r_{2,min}=R_{min}(180)+L(d_2)/2 \tag{11}$$

When planar image capturing is performed, the center positions $r_c$ of the detector panels $d_1,d_2$ are, in the ranges of $[\delta r_{1,min}, \delta r_{1,max}]$ and $[\delta r_{2,min}, \delta r_{2,max}]$, respectively, subject to repeated reciprocating movements along the tangential direction r or only one movement throughout the aforementioned range during a given collection time period. By means of gamma ray detection by the aforementioned operation, the areas where a gamma ray is not detected within the planes of the detector panels $d_1,d_2$ can be reduced as much as possible, and the sensitivity of the gamma ray detector can be enhanced.

Ninth Embodiment

Figure 19:
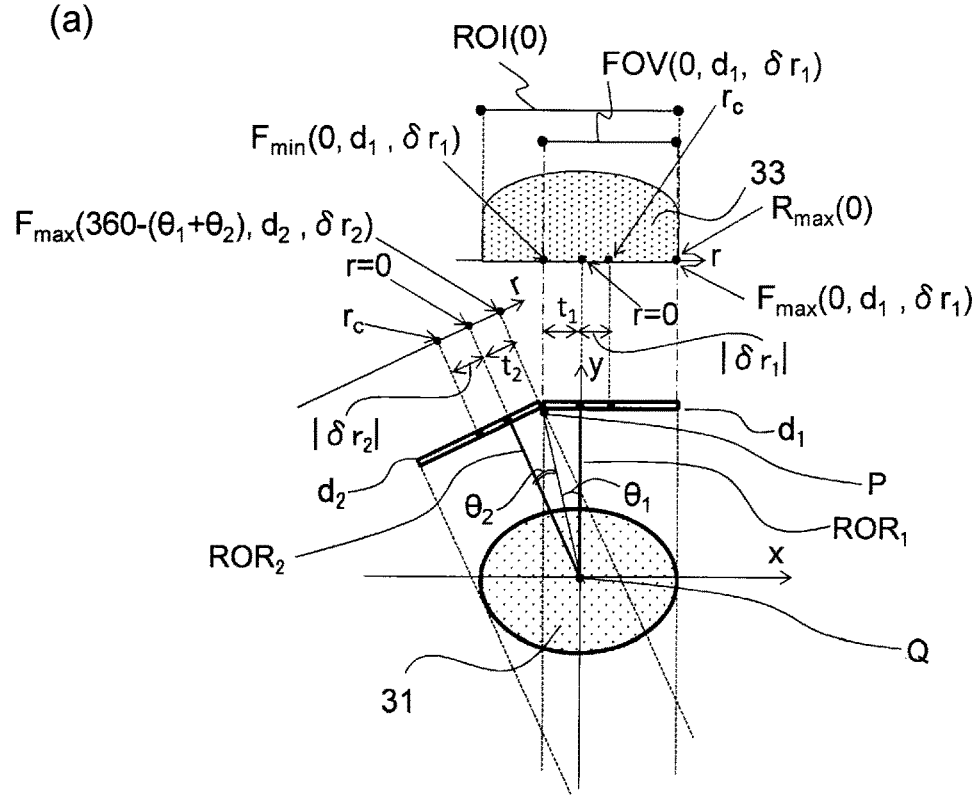
FIGS. 19(a) and 19(b) are diagrams illustrating other examples of planar image capturing.
Figure 19:
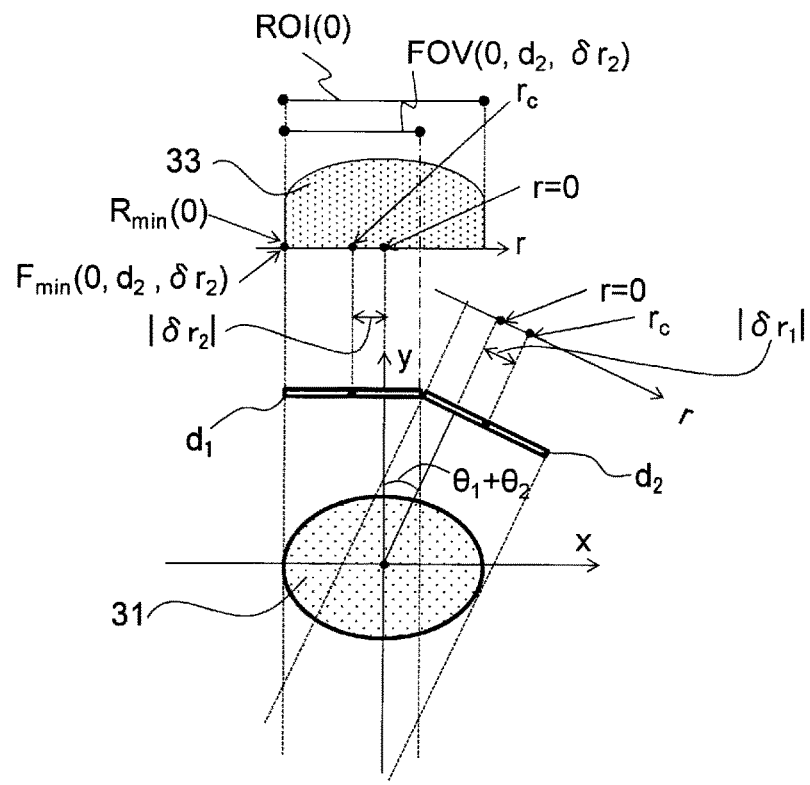

FIGS. 19(a) and 19(b) represent diagrams illustrating other examples of planar image capturing. FIG. 19(a) illustrates the positions of the detector panels $d_1,d_2$ at the beginning of capturing, and FIG. 19(b) illustrates the positions where the detector panels $d_1,d_2$ have rotated to their respective maximum angles. According to this embodiment, the two detector panels $d_1,d_2$ are used to capture the region of interest 31 at different angles. It is assumed that the lengths $L(d_1)$ and $L(d_2)$ of the capturing ranges of the detector panels $d_1,d_2$, respectively, in the tangential direction r are both shorter than the length of the projection image of the region of interest 31 in the tangential direction r and that ($L(d_1)+L(d_2)$), which is the sum of $L(d_1)$ and $L(d_2)$, is longer than the maximum value of the length of ROI(θ) ($=|R_{max}(θ)-R_{min}(θ)|$).

Based on projection image data obtained from, e.g., an X-ray CT apparatus, positional information ($R_{min}(0),R_{max}(0)$) of the end portion of the projection image of the region of interest 31 is acquired.

The text to follow addresses the situation illustrated in FIG. 19(a) where: the detector panel $d_1$ moves by $\delta r_1$ in the tangential direction r at a rotational position θ of 0 degree; and the position where the capturing range is maximum, $F_{max}(0,d_1,\delta r_1)$, is positioned near the position of the maximum value $R_{max}(0)$ at the end portion of the projection image of the region of interest 31. In this case, $\delta r_1$ can be calculated by equation (12):

$$\delta r_1=R_{max}(0)-L(d_1)/2 \tag{12}$$

The text to follow addresses the situation illustrated in FIG. 19(b) where: the detector panel $d_2$ moves by $\delta r_2$ in the tangential direction r at a rotational position θ0 of 0 degree; and the position where the capturing range is minimum, $F_{min}(0,d_2,\delta r_2)$, is positioned near the position of the minimum value $R_{min}(0)$ at the end portion of the projection image of the region of interest 31. In this case, $\delta r_2$ can be calculated by equation (13):

$$\delta r_2 = R_{min}(0) + L(d_2)/2 \qquad (13)$$

Also, it is assumed in the situation of FIG. 19(a) that the detector panel $d_2$ performs a rotational movement and nears to the detector panel $d_1$ positioned at a rotational position θ0 of 0 degree to an extent where the detector panel $d_1$ is not interfered. In this case, the position between the two end portions of the detector panel $d_1$ and the detector panel $d_2$ is denoted by P, and the line connecting point P and point Q, which is on the rotation axis, is defined as line P-Q. The angle between the line P-Q and the vertical line running down from the point Q to the detector panel $d_1$ is denoted by $θ_1$, and the angle between the line P-Q and the vertical line running down from the point Q to the detector panel $d_2$ is denoted by $θ_2$.

In this case, $t_1, t_2$, which denote the lengths of the detector panels $d_1, d_2$ of FIG. 19(a) in the tangential direction r, respectively, can be calculated by equations (14) and (15):

$$t_1 = L(d_1)/2 - |\delta r_1| \qquad (14)$$

$$t_2 = L(d_2)/2 - |\delta r_2| \qquad (15)$$

Also, where the rotational radiuses of the detector panels $d_1, d_2$ are denoted by $ROR_1$ and $ROR_2$, respectively, the angles $θ_1, θ_2$ can be calculated by equations (16) and (17):

$$θ_1 = \arctan(t_1/ROR_1) \qquad (16)$$

$$θ_2 = \arctan(t_2/ROR_2) \qquad (17)$$

The angle between the vertical line running down from the point Q to the detector panel $d_1$ and the vertical line running down from the point Q to the detector panel $d_2$, which is equal to $θ_1 + θ_2$, is denoted by $θ_{1-2}$. This angle $θ_{1-2}$ is assumed to be kept constant while the region of interest 31 is being captured.

As described above, this embodiment uses the two detector panels $d_1, d_2$ disposed adjacent to each other in the rotational direction. Specifically, detector panels $d_1, d_2$ are rotationally moved to capture the region of interest 31 while the value of $θ_{1-2}$ is kept constant. However, the rotational movement range is the range of the rotational position of FIG. 19(a) and the range of the rotational position of FIG. 19(b). Specifically, the detector panel $d_1$ and the detector panel $d_2$ move in the ranges of [0 degree, $θ_1 + θ_2$] and [360 degrees − ($θ_1 + θ_2$), 360 degrees], respectively. However, during actual capturing, the detector panels $d_1, d_2$ may repeatedly perform reciprocating movements or move throughout the aforementioned ranges once during a given collection time period.

According to this embodiment, as illustrated in FIGS. 19(a) and 19(b), the union of the capturing ranges of the detector panels $d_1, d_2$ at a rotational position of 0 degree is $FOV(0,d_1,\delta r_1) \cup FOV(0,d_2,\delta r_2)$, which contains ROI(0). In such a capturing method, the range of the projection image of the region of interest 31 at 0 degree is entirely covered in the tangential direction r. In addition, a projection image at a rotational position at a degree other than 0 degree is partially collected. Accordingly, the area where a gamma ray is not detected within the planes of the detector panels $d_1, d_2$ can be reduced as much as possible, and the sensitivity of a gamma ray detector can be enhanced.

The final planar image is acquired by means of successive approximation image reconstruction processing. In this embodiment, examples of using the two detector panels 11 are illustrated. However, use of the four detector panels 11 enables acquisition of a planar image at 0 degree and 180 degrees. The number of the detector panels 11 positioned near the rotational direction is not limited to two, and two or more detector panels 11 may be used. When two detector panels are disposed close to the rotational direction as in the case of this embodiment, use of a semiconductor detector with a field-of-view end portion whose dead space is small is suitable.

The present invention is not limited to the above-illustrated embodiments, and the scope of the present invention covers various modified embodiments. For example, the above-illustrated embodiments are illustrated in detail to describe the present invention in a readily understandable manner, and the present invention is not necessarily limited to embodiments with all the above-described features. A part of the features of a certain embodiment of the present invention may be replaced with a part of the features of another embodiment thereof. To a certain embodiment of the present invention, a part or all of the features of another embodiment thereof may be added.

REFERENCE SIGNS LIST

1 SPECT system
10 gantry
11, $d_1, d_2, d_3, d_4$ detector panel
12 data processing device
13 display device
14 bed
15 object
21 pixelated detector
23 detector substrate
24 ASIC substrate
25 integrated circuit
26 collimator
29 shield case
31 region of interest
32 rotation axis
33 projection image

The invention claimed is:
1. A radiation image capturing device comprising:
a plurality of detector panels each including a collimator that aligns an incident direction of a radioactive ray and a detector that detects the radioactive ray, the incident direction of which is aligned by the collimator;
a gantry mounted with the plurality of detector panels, the gantry rotating the mounted detector panels around a circumference, an object being substantially at a center of the circumference;
a computer coupled to the gantry; and
a tangential direction moving mechanism that moves, in a tangential direction of the rotational movement, the plurality of detector panels,
wherein the computer is programmed to:
calculate a first amount to move a first detector panel, of the plurality of detector panels, in the tangential direction based on a position where a size of a projection image of a region of interest of the object is a maximum in the tangential direction at a first rotational position and a length of the first detector panel in the tangential direction,
calculate a second amount to move a second detector panel, of the plurality of detectors, in the tangential direction based on a position where a size of a projection image of the region of interest is a minimum in the tangential direction at a second rotational position and a length of the second detector panel in the tangential direction, wherein, when the gantry rotates the detector panels around the entire circumference and a projection image of the region of interest at each of a plurality of rotational positions is captured by the plurality of the detector panels, at least the first detector panel and the second detector panel are moved in the tangential direction by the calculated first amount and second amount, respectively, so that a size of a union of a capturing range of the projection image captured by the plurality of the detector panels corresponds to a size of the region of interest, and wherein the computer is further programmed to use the projection image captured by each of the plurality of the detector panels that have performed the rotational movement and the tangential direction movement to reconstruct a transaxial image of the region of interest.

2. The radiation image capturing device according to claim 1, wherein the tangential direction movement of the first and second detector panels is performed at each rotational position.

3. The radiation image capturing device according to claim 1, wherein the tangential direction movement of the first and second detector panels is performed prior to each one rotational movement of the first and second detector panels around the entire circumference.

4. The radiation image capturing device according to claim 1, wherein the plurality of the detector panels are moved so that, at the each rotational position, a position where a size of the union of the capturing range in the tangential direction is minimum corresponds to a position where a size acquired by the second detector panel is minimum and that a position where the size of the union of the capturing range in the tangential direction is maximum corresponds to a position where the size acquired by the first detector panel is maximum.

5. The radiation image capturing device according to claim 1, wherein when the rotational movement of the first and second detector panels are performed around the entire circumference at a plurality of instances and capturing is performed at the each rotational position during movement of the detector panel in the tangential direction at each instance of the rotational movement, the first and second detector panels are moved in the tangential direction so that a position where a size of the union of the capturing range of the projection image captured at the each occasion of the rotational movement is minimum corresponds to a position where a size acquired by the second detector panel is minimum and that a position where the size of the union of the capturing range in the tangential direction is maximum corresponds to a position where the size acquired by the detector panel first detector panel is maximum.

6. A nuclear medicine diagnosis apparatus comprising the radiation image capturing device according to claim 1.

7. The radiation image capturing device according to claim 1, wherein the computer is further programmed to scan, in the tangential direction from a first position to a second position, a pixel value of the projection image at a rotational position and acquire, as the minimum position, the coordinate value in the tangential direction when the pixel value exceeds a specified threshold value.

8. A radiation image capturing device comprising:

a plurality of detector panels each including a collimator that aligns an incident direction of a radioactive ray and a detector that detects the radioactive ray, the incident direction of which is aligned by the collimator;

a gantry mounted with the plurality of detector panels, the gantry rotating the mounted detector panels around a circumference, and an object being substantially in a center of the circumference;

a computer coupled to the gantry; and a tangential direction moving mechanism that moves, in a tangential direction of the rotational movement, the detector panels mounted on the gantry, wherein the computer is programmed to:

calculate a first amount to move a first detector panel, of the plurality of detector panels, in the tangential direction based on a position where a size of a projection image of a region of interest of an object is a maximum in the tangential direction at a first rotational position and a length of the first detector panel in the tangential direction, calculate a second amount to move a second detector panel, of the plurality of detectors, in the tangential direction based on a position where a size of a projection image of the region of interest is a minimum in the tangential direction at a second rotational position and a length of the second detector panel in the tangential direction, wherein, when the tangential direction moving mechanism moves the detector panels in the tangential direction and captures a projection image of the region of interest at a plurality of movement positions, the at least the first detector panel and the second detector panel are moved in the tangential direction by the calculated first amount and second amount, respectively, so that a union of a capturing range of the projection image captured at each movement position corresponds to a size of the region of interest, and wherein the computer is further programmed to use the projection image captured by the detector panels that have performed the tangential direction movement to reconstruct a planar image of the region of interest.

9. A radiation image capturing method performed by a radiation image capturing device, the radiation image capturing device comprising:

a plurality of detector panels including a collimator that aligns an incident direction of a radioactive ray and a detector that detects the radioactive ray, the incident direction of which is aligned by the collimator, a gantry mounted with the plurality of the detector panels, the gantry rotating the plurality of the mounted detector panels around a circumference, and an object is substantially in a center of a circumference, a computer coupled to the gantry; and a tangential direction moving mechanism that moves, in a tangential direction of the rotational movement, the plurality of the detector panels mounted on the gantry, the radiation image capturing method comprising the steps of:

calculating, by the computer, a first amount to move a first detector panel, of the plurality of detector panels, in the tangential direction based on a position where a size of a projection image of a region of interest of an object is a maximum in the tangential direction at a first rotational position and a length of the first detector panel in the tangential direction, calculating, by the computer, a second amount to move a second detector panel, of the plurality of detectors, in the tangential direction based on a position where a size of a projection image of the region of interest is a minimum in the tangential direction at a second rotational position and a length of the second detector panel in the tangential direction, moving at least the first detector panel and the second detector panel in the tangential direction by the calculated first amount and second amount, respectively, so that a size of a union of a capturing range of the projection image captured by the at least the first detector panel and the second detector panel corresponds to a size of the region of interest when the gantry performs the rotational movement of the detector panels around the entire circumference of the object and a projection image of the region of interest at each rotational position is captured by the plurality of the detector panels; and reconstructing a transaxial image of the region of interest using a projection image captured by the plurality of the detector panels that have performed the rotational movement and tangential direction movement.

10. The radiation image capturing method according to claim 9, wherein
the tangential direction movement of the first and second detector panels is performed at each rotational position.

11. The radiation image capturing method according to claim 9, wherein
the tangential direction movement of the first and second detector panels is performed prior to each one rotational movement of the first and second detector panels around the entire circumference of the object.

12. The radiation image capturing method according to claim 9,
the radiation image capturing method performed by the radiation image capturing device further comprising the step of:
moving the plurality of the detector panels so that, at the each rotational position, a position where a size of the union of the capturing range in the tangential direction is minimum corresponds to a position where a size acquired by the second detector is minimum and that a position where the size of the union of the capturing range in the tangential direction is maximum corresponds to a position where the size acquired by the first detector is maximum.

13. The radiation image capturing method according to claim 9,
the radiation image capturing method performed by the radiation image capturing device further comprising the step of:
when the rotational movement of the first and second detector panels are performed around the entire circumference of the object on a plurality of instances and capturing is performed at the each rotational position during movement of the detector panel in the tangential direction at each instance of the rotational movement, moving the first and second detector panels in the tangential direction so that a position where a size of the union of the capturing range of the projection image captured at the each occasion of the rotational movement is minimum corresponds to a position where a size acquired by the projection image acquisition means is minimum and that a position where the size of the union of the capturing range in the tangential direction is maximum corresponds to a position where the size acquired by the projection image acquisition means is maximum.

14. A radiation image capturing method performed by a radiation image capturing device,
the radiation image capturing device comprising:
a plurality of detector panels each including a collimator that aligns an incident direction of a radioactive ray and a detector that detects the radioactive ray, the incident direction of which is aligned by the collimator,
a gantry mounted with the plurality of detector panels, the gantry rotating the detector panels around a circumference, and an object is substantially in a center of the circumference,
a tangential direction moving mechanism that moves, in a tangential direction of the rotational movement, the detector panels mounted on the gantry,
the radiation image capturing method comprising the steps of:
calculating, by the computer, a first amount to move a first detector panel, of the plurality of detector panels, in the tangential direction based on a position where a size of a projection image of a region of interest of an object is a maximum in the tangential direction at a first rotational position and a length of the first detector panel in the tangential direction,
calculating, by the computer, a second amount to move a second detector panel, of the plurality of detectors, in the tangential direction based on a position where a size of a projection image of the region of interest is a minimum in the tangential direction at a second rotational position and a length of the second detector panel in the tangential direction,
when the tangential direction moving mechanism moves the detector panel in the tangential direction and captures a projection image of the region of interest at a plurality of movement positions, moving at least the first detector panel and the second detector panel in the tangential direction by the calculated first amount and second amount, respectively, so that a size of a union of a capturing range of the projection image captured at each movement position corresponds to a size of the region of interest; and
reconstructing a planar image of the region of interest by collecting projection image data captured by the plurality of the detector panels that have performed the tangential direction movement.

* * * * *